(12) United States Patent
Shimizu et al.

(10) Patent No.: US 12,193,745 B2
(45) Date of Patent: Jan. 14, 2025

(54) CLOSE-UP IMAGING DEVICE

(71) Applicant: OUI INC., Tokyo (JP)

(72) Inventors: Eisuke Shimizu, Tokyo (JP); Hiroyuki Yazu, Tokyo (JP); Naohiko Aketa, Tokyo (JP)

(73) Assignee: OUI INC., Tokyo (JP)

( * ) Notice: Subject to any disclaimer, the term of this patent is extended or adjusted under 35 U.S.C. 154(b) by 1113 days.

(21) Appl. No.: 16/964,822

(22) PCT Filed: Jan. 28, 2019

(86) PCT No.: PCT/JP2019/002824
§ 371 (c)(1),
(2) Date: Jul. 24, 2020

(87) PCT Pub. No.: WO2019/146792
PCT Pub. Date: Aug. 1, 2019

(65) Prior Publication Data
US 2021/0059522 A1 Mar. 4, 2021

(30) Foreign Application Priority Data
Jan. 26, 2018 (JP) .................................. 2018-011632

(51) Int. Cl.
*A61B 3/117* (2006.01)
*A61B 3/14* (2006.01)
*A61B 3/135* (2006.01)

(52) U.S. Cl.
CPC ................ *A61B 3/117* (2013.01); *A61B 3/14* (2013.01); *A61B 3/135* (2013.01)

(58) Field of Classification Search
CPC .. H04N 23/55; H04N 1/02815; H04N 1/0282; H04N 1/02885; H04N 1/195;
(Continued)

(56) References Cited

U.S. PATENT DOCUMENTS

2005/0200707 A1  9/2005  Yogesan et al.
2005/0270484 A1  12/2005  Maeda et al.
(Continued)

FOREIGN PATENT DOCUMENTS

JP  2004-081387 A  3/2004
JP  2005-524462 A  8/2005
(Continued)

OTHER PUBLICATIONS

International Search Report for PCT/JP2019/002824 dated, Apr. 16, 2019 (PCT/ISA/210).
(Continued)

*Primary Examiner* — Brandi N Thomas
(74) *Attorney, Agent, or Firm* — Sughrue Mion, PLLC

(57) ABSTRACT

To provide a close-up imaging device whereby both imaging of an anterior eye and imaging of an eye ground can easily be performed by attaching the device to a mobile terminal such as a smartphone. The above-described problem is solved by a close-up imaging device (1B) detachably mounted to a mobile terminal (9) equipped with a light source (92) and a camera lens (91) for imaging, comprising a color filter member (97) detachably provided above the light source (92), and a convex lens member (93) detachably provided above the camera lens (91). Imaging, of an anterior eye is performed by removing the color filter member (97) and attaching the convex lens member (93), and observation of an injury of the anterior eye is performed by attaching the color filter member (97) and the convex lens member (93). The close-up imaging device (1B) may further detachably comprise a slit light forming member that forms light from the light source (92) into slit light by a cylindrical lens, and a tubular member including a convex lens at a tip end thereof.

10 Claims, 25 Drawing Sheets

(58) Field of Classification Search
CPC ............ H04N 1/19594; H04N 23/555; H04N 23/651; H04N 25/441; H04N 25/61; H04N 25/625; H04N 25/73; H04N 1/00132; H04N 1/00135; H04N 1/00137; H04N 1/00148; H04N 1/00161; H04N 1/00167; H04N 1/00188; H04N 1/00249; H04N 1/00267; H04N 1/0027; H04N 1/32128; H04N 2201/3226; H04N 2201/3242; H04N 2201/3274; H04N 2201/3278; H04N 23/56; H04N 23/665; H04N 23/74; H04N 25/42; H04N 25/53; H04N 25/745; H04N 3/1568; A61B 3/10; A61B 3/12; A61B 3/14; A61B 3/113; A61B 3/1208; A61B 3/145; A61B 1/00096; A61B 1/00101; A61B 1/00124; A61B 1/00188; A61B 1/00193; A61B 1/042; A61B 1/043; A61B 1/05; A61B 1/051; A61B 1/06; A61B 1/24; A61B 2090/309; A61B 2560/0443; A61B 3/117; A61B 3/125; A61B 5/0088; A61B 5/6898; G03B 17/12; G03B 17/565; G03B 11/045; G03B 17/563; G03B 21/06; G03B 21/132; G03B 17/04; G03B 17/566; G03B 35/10; G03B 11/00; G03B 15/05; G03B 17/56; G03B 19/02; G03B 19/10; G03B 2215/0539; G02B 21/00; G02B 21/06; G02B 6/353; G02B 6/3558; G02B 13/0095; G02B 15/142; G02B 15/144109; G02B 21/08; G02B 21/16; G02B 23/2484; G02B 27/646; G02B 7/006; G02B 7/022; G02B 7/14; G02B 21/0032; G02B 21/0048; G02B 21/0076; G02B 21/02; G02B 21/04; G02B 21/24; G02B 21/248; G02B 21/34; G02B 21/361; G02B 21/367; G02B 23/18; G02B 7/02; G02B 7/04

See application file for complete search history.

(56) References Cited

U.S. PATENT DOCUMENTS

| | | | |
|---|---|---|---|
| 2014/0009737 A1 | 1/2014 | Kweon | |
| 2016/0295109 A1 | 10/2016 | Henriksen | |
| 2016/0367135 A1* | 12/2016 | Myung | ................ A61B 3/1208 |
| 2017/0280996 A1 | 10/2017 | Myung et al. | |

FOREIGN PATENT DOCUMENTS

| | | |
|---|---|---|
| JP | 2014-192876 A | 10/2014 |
| JP | 3197418 U | 5/2015 |
| JP | 2016-523122 A | 8/2016 |
| JP | 2016-524483 A | 8/2016 |
| JP | 2017-501005 A | 1/2017 |
| JP | 6118477 B1 | 4/2017 |
| JP | 2017-121320 A | 7/2017 |

OTHER PUBLICATIONS

Written Opinion of the International Searching Authority for PCT/JP2019/002824 dated, Apr. 16, 2019 (PCT/ISA/237).

* cited by examiner

Fig. 17B

| Body Weight weeks | Normal | non-GVHD | GVHD | P-value* Normal vs non-GVHD | Normal vs GVHD | Non-GVHD vs GVHD |
|---|---|---|---|---|---|---|
| 8 | 19.20 ± 0.75 | 18.82 ± 0.93 | 18.86 ± 0.93 | 0.524 | 0.651 | 0.999 |
| 9 | 20.04 ± 1.19 | 17.26 ± 0.63 | 17.04 ± 0.89 | 0.016 | 0.016 | 0.714 |
| 10 | 20.68 ± 1.16 | 17.66 ± 0.91 | 18.02 ± 1.12 | 0.016 | 0.032 | 0.746 |
| 11 | 20.84 ± 1.37 | 19.30 ± 0.64 | 18.04 ± 1.63 | 0.095 | 0.032 | 0.286 |
| 12 | 21.30 ± 1.41 | 19.68 ± 1.00 | 17.88 ± 2.13 | 0.071 | 0.032 | 0.151 |

Data are shown by mean ± SD. Female, BALB/cCrSlc mice, n = 5.
*P value: Mann-Whitney U test.

Fig. 18A

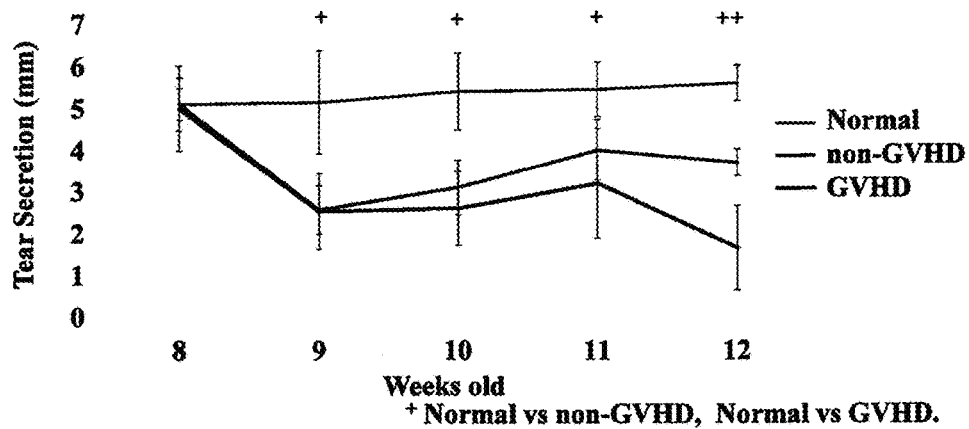

+ Normal vs non-GVHD, Normal vs GVHD.

Fig. 18B

| Tear Secretion weeks | Normal | non-GVHD | GVHD | P-value* Normal vs non-GVHD | Normal vs GVHD | Non-GVHD vs GVHD |
|---|---|---|---|---|---|---|
| 8 | 5.10 ± 0.63 | 5.10 ± 0.38 | 5.00 ± 1.02 | 0.984 | 0.968 | 0.999 |
| 9 | 5.15 ± 1.23 | 2.57 ± 0.58 | 2.53 ± 0.91 | 0.008 | 0.016 | 0.999 |
| 10 | 5.40 ± 0.91 | 3.10 ± 0.65 | 2.60 ± 0.88 | 0.008 | 0.008 | 0.079 |
| 11 | 5.45 ± 0.65 | 4.00 ± 0.73 | 3.20 ± 1.32 | 0.016 | 0.024 | 0.421 |
| 12 | 5.60 ± 0.42 | 3.70 ± 0.33 | 1.65 ± 1.01 | 0.008 | 0.008 | 0.008 |

Data are shown by mean ± SD. Female, BALB/cCrSlc mice, n = 5.
*P value: Mann-Whitney U test.

Fig. 19A
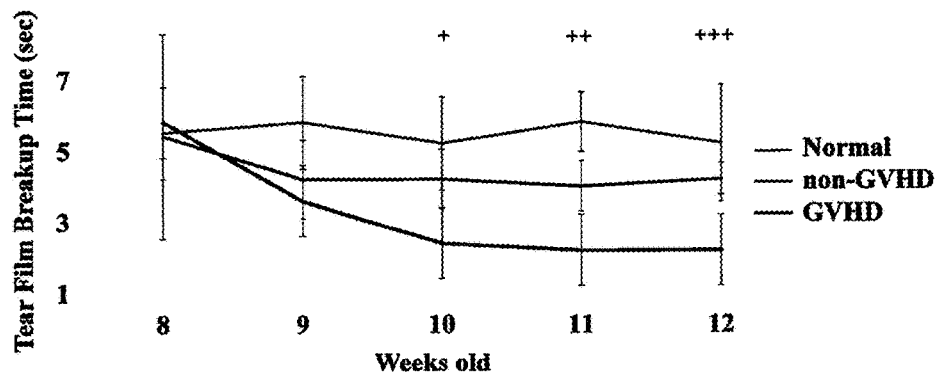
+ Normal vs GVHD. ++Normal vs non-GVHD, Normal vs GVHD, Non-GVHD vs GVHD.
+++Normal vs GVHD, Non-GVHD vs GVHD. P<0.05.
Fig. 19B
| Tear Film Breakup Time weeks | Normal | non-GVHD | GVHD | P-value* Normal vs non-GVHD | Normal vs GVHD | Non-GVHD vs GVHD |
|---|---|---|---|---|---|---|
| 8 | 5.50 ± 1.29 | 5.40 ± 2.88 | 5.80 ± 2.17 | 0.754 | 0.754 | 0.952 |
| 9 | 5.80 ± 1.30 | 4.20 ± 1.10 | 3.60 ± 1.14 | 0.103 | 0.056 | 0.556 |
| 10 | 5.20 ± 1.30 | 4.20 ± 0.84 | 2.40 ± 1.14 | 0.333 | 0.024 | 0.056 |
| 11 | 5.80 ± 0.84 | 4.00 ± 0.71 | 2.20 ± 1.10 | 0.024 | 0.008 | 0.040 |
| 12 | 5.20 ± 1.64 | 4.20 ± 0.45 | 2.20 ± 0.84 | 0.405 | 0.008 | 0.008 |
Data are shown by mean ± SD. Female, BALB/cCrSlc mice, n = 5.
*P value: Mann-Whitney U test.
Fig. 20
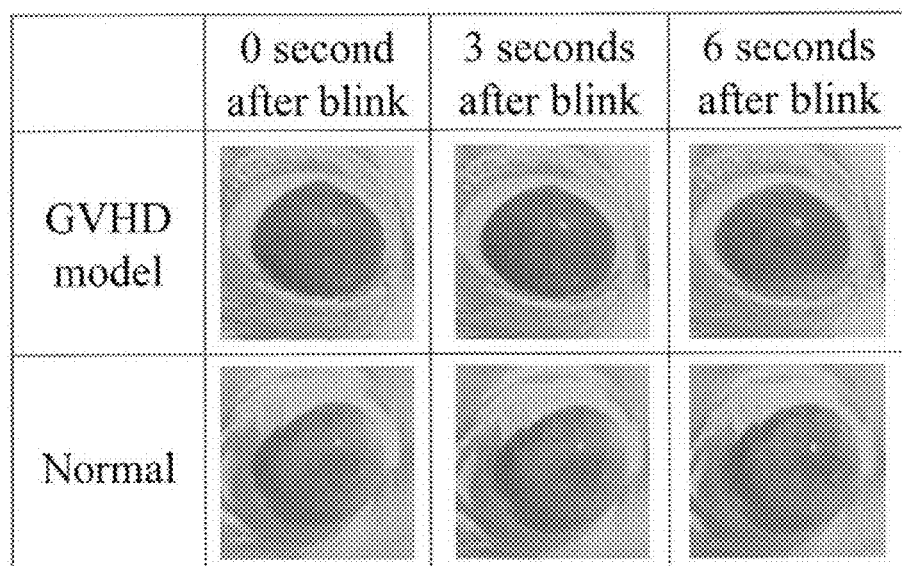

Fig. 21A
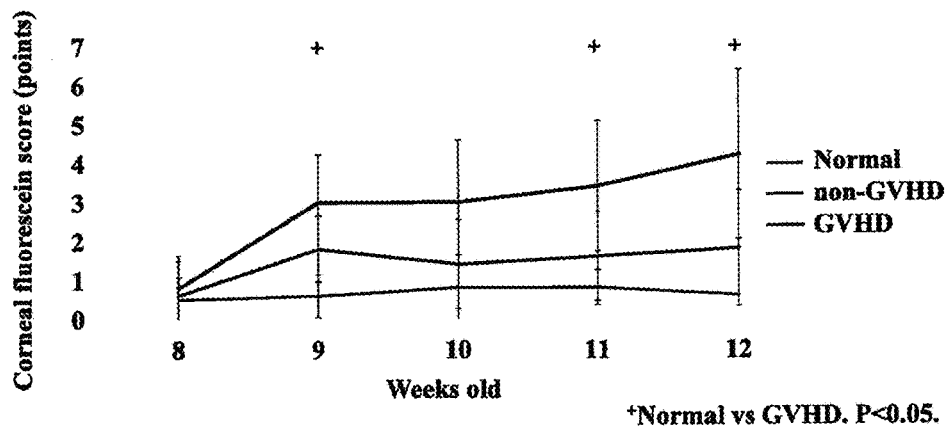
⁺Normal vs GVHD. P<0.05.
Fig. 21B
| Corneal Fluorescein Score weeks | Normal | non-GVHD | GVHD | P-value* | | |
|---|---|---|---|---|---|---|
| | | | | Normal vs non-GVHD | Normal vs GVHD | Non-GVHD vs GVHD |
| 8 | 0.50 ± 0.58 | 0.60 ± 0.89 | 0.80 ± 0.84 | 0.999 | 0.810 | 0.921 |
| 9 | 0.60 ± 0.55 | 1.80 ± 0.84 | 3.00 ± 1.22 | 0.079 | 0.008 | 0.191 |
| 10 | 0.80 ± 0.84 | 1.40 ± 1.14 | 3.00 ± 1.58 | 0.532 | 0.056 | 0.175 |
| 11 | 0.80 ± 0.45 | 1.60 ± 1.14 | 3.40 ± 1.67 | 0.318 | 0.008 | 0.135 |
| 12 | 0.60 ± 0.55 | 1.80 ± 1.48 | 4.20 ± 2.17 | 0.206 | 0.032 | 0.119 |
Data are shown by mean ± SD. Female, BALB/cCrSlc mice, n = 5.
*P value: Mann-Whitney U test.
Fig. 22A
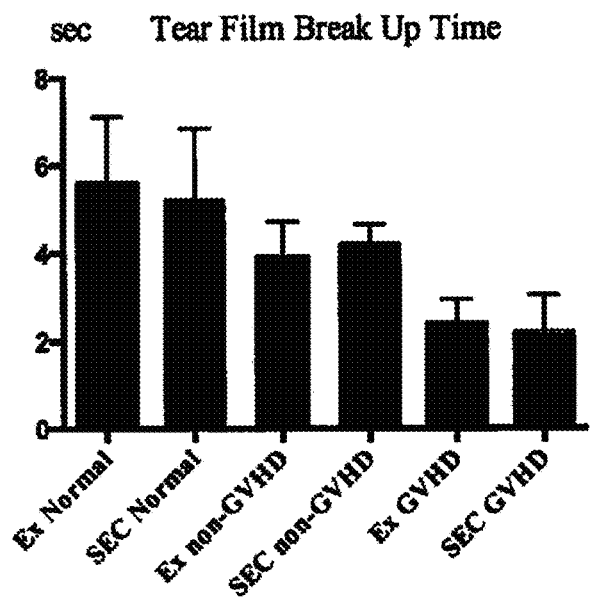

Fig. 22B
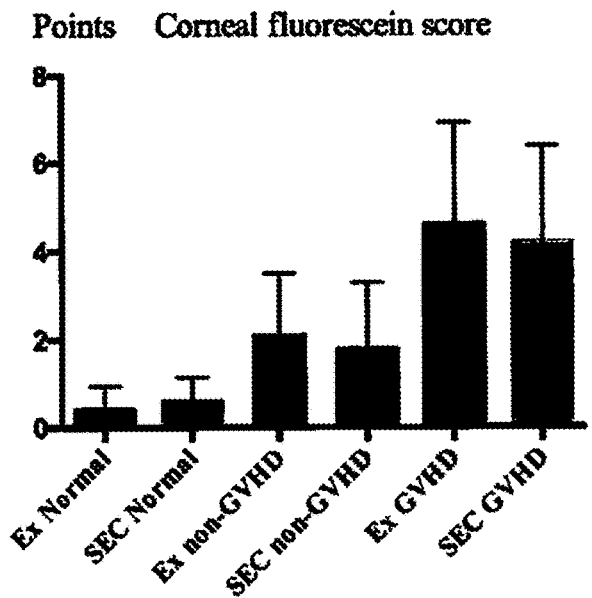
Fig. 22C
|  | | Normal | non-GVHD | GVHD | Normal | P-value*<br>non-GVHD | GVHD |
|---|---|---|---|---|---|---|---|
| TFBUT | Ex | 5.60 ± 1.52 | 4.00 ± 0.71 | 2.40 ± 0.55 | 0.500 | 0.999 | 0.999 |
|  | SEC | 5.20 ± 1.64 | 4.20 ± 0.45 | 2.20 ± 0.84 |  |  |  |
| CFL | Ex | 0.40 ± 0.55 | 2.20 ± 1.30 | 4.60 ± 2.30 | 0.999 | 0.750 | 0.500 |
|  | SEC | 0.60 ± 0.55 | 1.80 ± 1.48 | 4.20 ± 2.17 |  |  |  |
Data are shown by mean ± SD. Female, BALB/cCrSlc mice, n = 5.
Ex: Existing device. SEC: Smart Eye Camera.
*P value: Existing device vs Smart Eye Camera. Wilcoxon test.
Fig. 23A
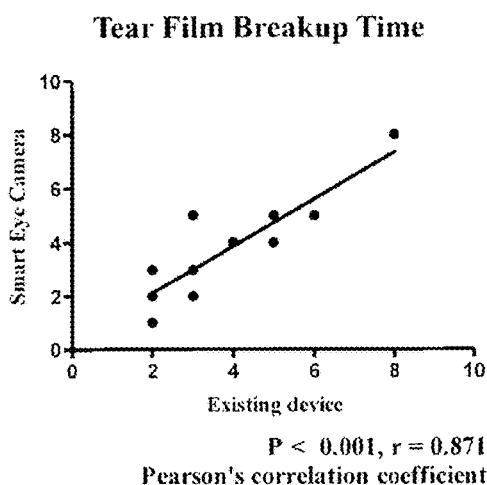
$P < 0.001, r = 0.871$
Pearson's correlation coefficient

|  |  | Normal | non-GVHD | GVHD | P-value* | | |
|---|---|---|---|---|---|---|---|
|  |  |  |  |  | Normal | non-GVHD | GVHD |
| TS | R | 5.60 ± 0.42 | 3.70 ± 0.33 | 1.65 ± 1.01 | 0.381 | 0.999 | 0.984 |
|  | L | 5.20 ± 0.57 | 3.70 ± 0.41 | 1.75 ± 1.05 |  |  |  |
| TFBUT | R | 5.20 ± 1.64 | 4.20 ± 0.45 | 2.20 ± 0.84 | 0.999 | 0.278 | 0.635 |
|  | L | 5.40 ± 1.55 | 3.60 ± 0.55 | 1.80 ± 0.45 |  |  |  |
| CFS | R | 0.60 ± 0.55 | 1.80 ± 1.48 | 4.20 ± 2.17 | 0.524 | 0.881 | 0.999 |
|  | L | 0.40 ± 0.89 | 1.80 ± 0.45 | 4.20 ± 1.48 |  |  |  |

Data are shown by mean ± SD. Female, BALB/cCrSlc mice, n = 5.
*P value: Right vs Left. Mann-Whitney U test.

Fig. 28D
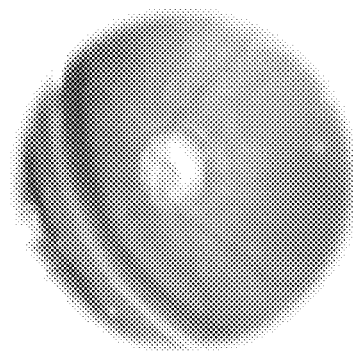
Fig. 29
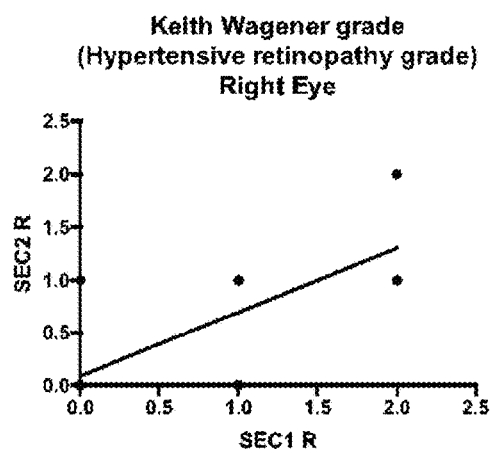
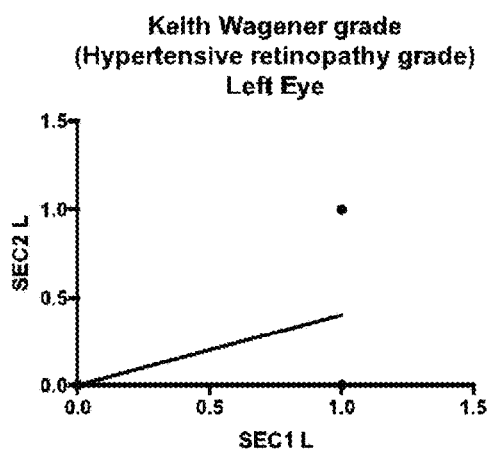

CLOSE-UP IMAGING DEVICE

FIELD OF THE INVENTION

The present invention relates to a close-up imaging device utilized for diagnosing a lesion of an anterior eye or an eye ground or the like, and used by being mounted to a portable mobile terminal, such as a smartphone.

BACKGROUND ART

To perform an eye examination, a specialized magnifier is required. A doctor carries out a process of performing an examination using the magnifier, obtaining findings to conduct an evaluation, and making a diagnosis to provide treatment. In an ophthalmic outpatient clinic, a slit lamp biomicroscope is used. However, because the slit lamp biomicroscope is large, heavy, and expensive, conventionally a handheld slit lamp biomicroscope has been widely used when simplicity is required or at an ophthalmic examination site other than an outpatient clinic, such as bedside.

However, with a handheld slit lamp biomicroscope operation is difficult and therefore the information obtained is less, and it is possible to observe only the anterior eye and not the eye ground, and impossible to record images. Further, with a handheld slit lamp biomicroscope, it takes time to obtain findings, and the number of patients or the like that can be examined at one time is only one. Furthermore, the handheld slit lamp biomicroscope has many problems such as being heavy due to inclusion of a light source.

As prior art for solving the above-described problems, for example, close-up imaging devices and ultra-close-up imaging devices, each having a lighting function and capturing an image with a smartphone fixed onto a stand with a light source have been proposed (refer to, for example, Patent Document 1 and Patent Document 2). Further, for example, ophthalmoscopes including a system or an application for storing an image obtained on the basis of an image acquiring technique have been proposed (refer to, for example, Patent Document 3). Furthermore, for example, wide-field retinal image acquiring systems and methods for capturing and analyzing an image of a retina using a smartphone have been proposed (refer to, for example, Patent Document 4).

PRIOR ART DOCUMENTS

Patent Documents
Patent Document 1: Japanese Laid-Open Patent Application No. 2017-121320Patent Document 2: Utility Model Registration No. 3197418Patent Document 3: Japanese Translation of PCT International Application No. 2016-524483Patent Document 4: Japanese Translation of PCT International Application No. 2017-501005

SUMMARY OF THE INVENTION

Problems to be Solved by the Invention

However, the devices described in the above-described Patent Document 1 and Patent Document 2 remain problematic in that they are heavy due to inclusion of a light source, do not permit observation of both the anterior eye and the eye ground from an irradiation angle of light from the light source, and the like. Further, the device described, in the above-described Patent Document 3 is problematic in that it does not have a close-up function during anterior eye imaging, details of the light source are not described and thus an image cannot actually be acquired, and the like. Furthermore, the device described in the above-described Patent Document 4 is problematic in that it puts only an image of the retina into focus, anterior eye imaging is not performed, and the like.

Further, the conventional devices described in each of the patent documents described above remain macro-problematic in that findings cannot be obtained unless the examination is performed by a skilled person, evaluation must be performed at the examination site, and the like, and remain problematic in that they cannot be used for research and the like. Furthermore, none of the devices described in each of the patent documents described above has been commercialized.

The present invention is made to resolve the above-described problems, and an object of the present invention is to provide a close-up imaging device whereby both imaging of an anterior eye and imaging of an eye ground can easily be performed by attaching the device to a mobile terminal such as a smartphone.

Means for Solving the Problems

The close-up imaging device according to the present invention is a device for observing and capturing an image of an anterior eye and an eye ground, and includes a close-up imaging device of a first embodiment for observing and capturing an image of the anterior eye and the eye ground through different routes, and a close-up imaging device of a second embodiment for observing and capturing an image of the anterior eye and the eye ground by combining detachable members.

(1) A close-up imaging device according to a first embodiment of the present invention is a close-up imaging device detachably mounted to a mobile terminal equipped with a light source and a camera lens for imaging, and comprises a first optical path forming part that forms a first optical path by light from the light source, a second optical path forming part that forms a second optical path, different from the first optical path, by the light from the light source, and an optical path switching part that switches between the first optical path and the second optical path by the light from the light source. According to this invention, it is possible to observe and capture an image of the eye ground in the first optical path, and observe and capture an image of the anterior eye in the second optical path.

In the close-up imaging device according to the first embodiment of the present invention, the optical path switching part includes a reflecting member capable of reflecting the light from the light source, the first optical path is formed by light from the light source not being reflected by the reflecting member, and the second optical path is formed by light from the light source being reflected by the reflecting member.

In the close-up imaging device according to the first embodiment of the present invention, the second optical path is provided with one or two or more parts selected from (a) a focus adjusting part for focusing the light from the light source of the second optical path on an irradiated object irradiated with the light, (b) an irradiation position adjusting part capable of adjusting an irradiation position on an irradiated object irradiated with the light, and (c) a slit forming part that forms the light from the light source into linear light. According to these aspects of this invention, observation and imaging of the anterior eye performed utilizing the second optical path can be more accurately performed.

(2) The close-up imaging device according to a second embodiment of the present invention is a close-up imaging device detachably mounted to a mobile terminal equipped with a light source and a camera lens for imaging, and comprises a color filter member detachably provided above the light source, and a convex lens member detachably provided above the camera lens. Imaging of an anterior eye is performed by removing the color filter member and attaching the convex lens member, and observation of an injury of the anterior eye is performed by attaching the color filter member and the convex lens member. According to this invention, imaging of the anterior eye and observation of an injury can be performed by attaching and detaching the color filter member with the convex lens member attached.

In the close-up imaging device according to the second embodiment of the present invention, the color filter member and the convex lens member are plate-shaped members, and the color filter member is attached and detached from above the light source or the convex lens member is attached and detached from above the camera lens for imaging by sliding the plate-shaped members.

The close-up imaging device according to the second embodiment of the present invention further detachably comprises a slit light forming member that forms light from the light source into slit light by a cylindrical lens. According to this invention, observation and imaging of an internal structure of the anterior eye can be performed in more detail by the slit light formed by the cylindrical lens.

In the close-up imaging device according to the second embodiment of the present invention, the slit light forming member includes a first reflecting mirror and a second reflecting mirror that reflect the light from the light source, and a slit part that allows the light reflected by the first reflecting mirror and the second reflecting mirror to pass therethrough, and the light that passes through the slit part becomes slit light by the cylindrical lens.

In the close-up imaging device according to the second embodiment of the present invention, the close-up imaging device further detachably comprises a tubular member including a convex lens at a tip end thereof. According to this invention, a focal length from the eye ground can be adjusted to and maintained in an appropriate state by the tubular member. As a result, observation and imaging of the eye ground can be performed.

In the close-up imaging device according to the second embodiment of the present invention, the tubular member includes a color filter member and a polarizing filter in an optical path of outward light emitted from the light source, and another polarizing filter in an optical path of inward light reflected by the eye ground. According to this invention, it is possible to prevent the outward light and the inward light from interfering with each other inside the tubular member. As a result, observation and imaging of the eye ground by the inward light can be clearly performed.

Effect of the Invention

According to the present invention, it is possible to provide a close-up imaging device whereby both imaging of an anterior eye and imaging of an eye ground can easily be performed by attaching the device to a mobile terminal such as a smartphone.

BRIEF DESCRIPTION OF THE DRAWINGS

FIG. 17B is a table of progress of body weight by group.

FIG. 18A is a graph showing results obtained by measuring a relationship between age (weeks old) and tear secretion (TS) volume of mice, and FIG. 18B is a table of progress of continuing tear secretion (TS) by group.

FIG. 19A is a graph showing results obtained by measuring a relationship between age (weeks old) and tear film break-up time (TFBUT) of mice, and FIG. 19B is a table of progress of TFBUT by group.

FIG. 20 shows photographs of continuous tear films stained with a fluorescein solution, the upper row being examples of a GVHD group in which the tear film is broken in three seconds, and the lower row being examples of a normal group in which the tear film is stabilized in three seconds and collapsed in six seconds.

FIG. 21A is a graph showing results obtained by measuring a relationship between age (weeks old) and continuous corneal fluorescein score (CFS) of mice, and FIG. 21B is a table of progress of CFS by group.

FIGS. 22A to 22C show results of comparing the IFBUTs and CFSs of the close-up imaging device according to the present invention and the existing device, FIG. 22A being a graph of TFBUT and FIG. 22B being a graph of CFS.

FIGS. 23A and 23B are graphs showing a correlation between the close-up imaging device according to the present invention and the existing device, FIG. 23A being a graph of TFBUT and FIG. 23B being a graph of CFS.

FIGS. 28A to 28D show imaging results of eye grounds, FIG. 28A being a normal eye ground, FIG. 28B being hypertensive retinopathy, FIG. 28C being retina thinning, and FIG. 28D being optic disc cupping and expansion (suspected glaucoma).

FIG. 29 is a correlation between doctors of hypertensive retinopathy evaluated by the smart eye camera.

EMBODIMENTS OF THE INVENTION

A close-up imaging device according to the present invention will now be described with reference to the drawings. The present invention is not limited to the embodiments described below, and includes modifications and applications thereof. A close-up imaging device 1 according to the present invention includes a first embodiment and a second embodiment below. Hereinafter, each embodiment will be described in detail.

First Embodiment

Figure 1:
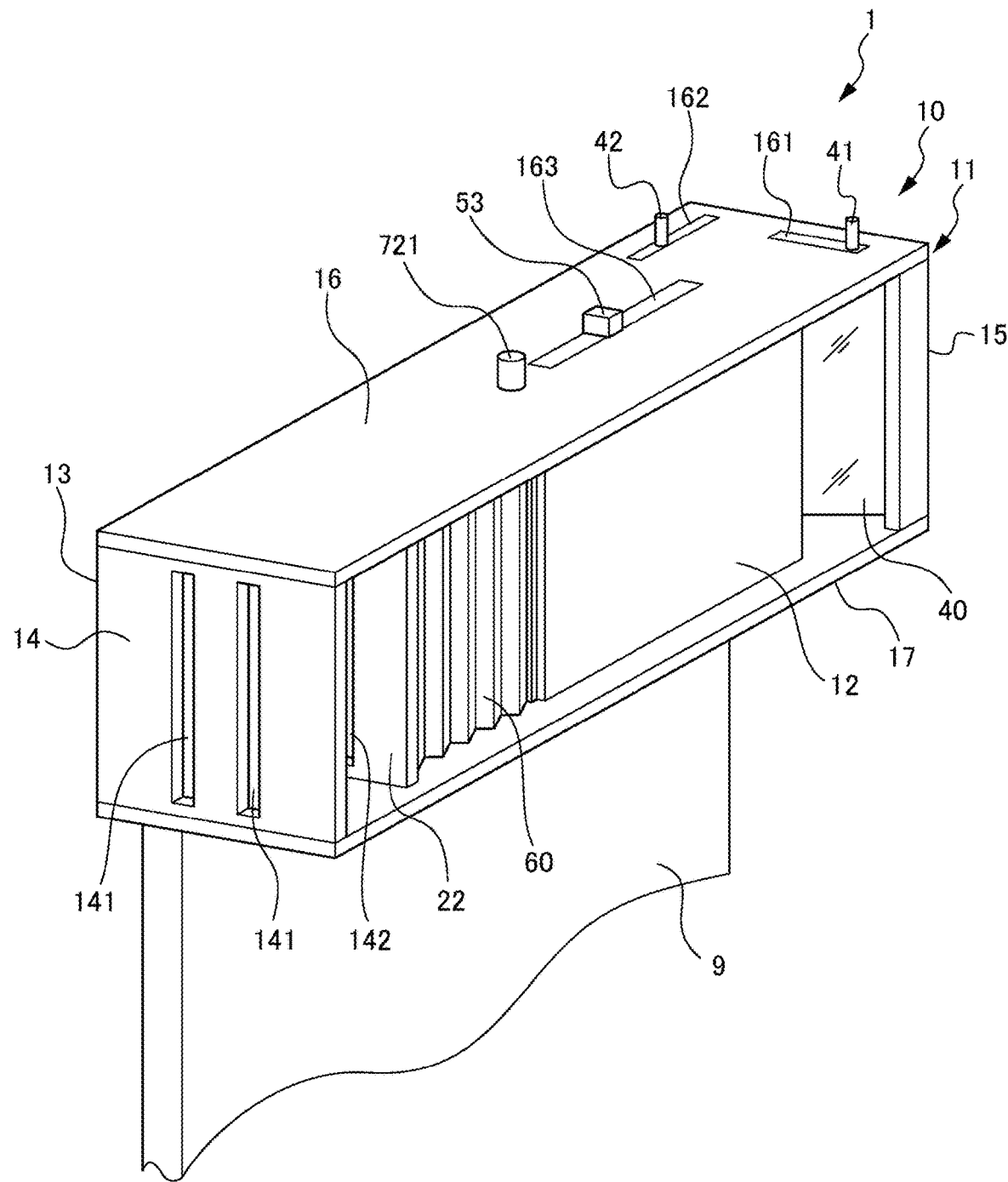
FIG. 1 is a perspective view illustrating a first embodiment of a close-up imaging device according to the present invention.
Figure 2:
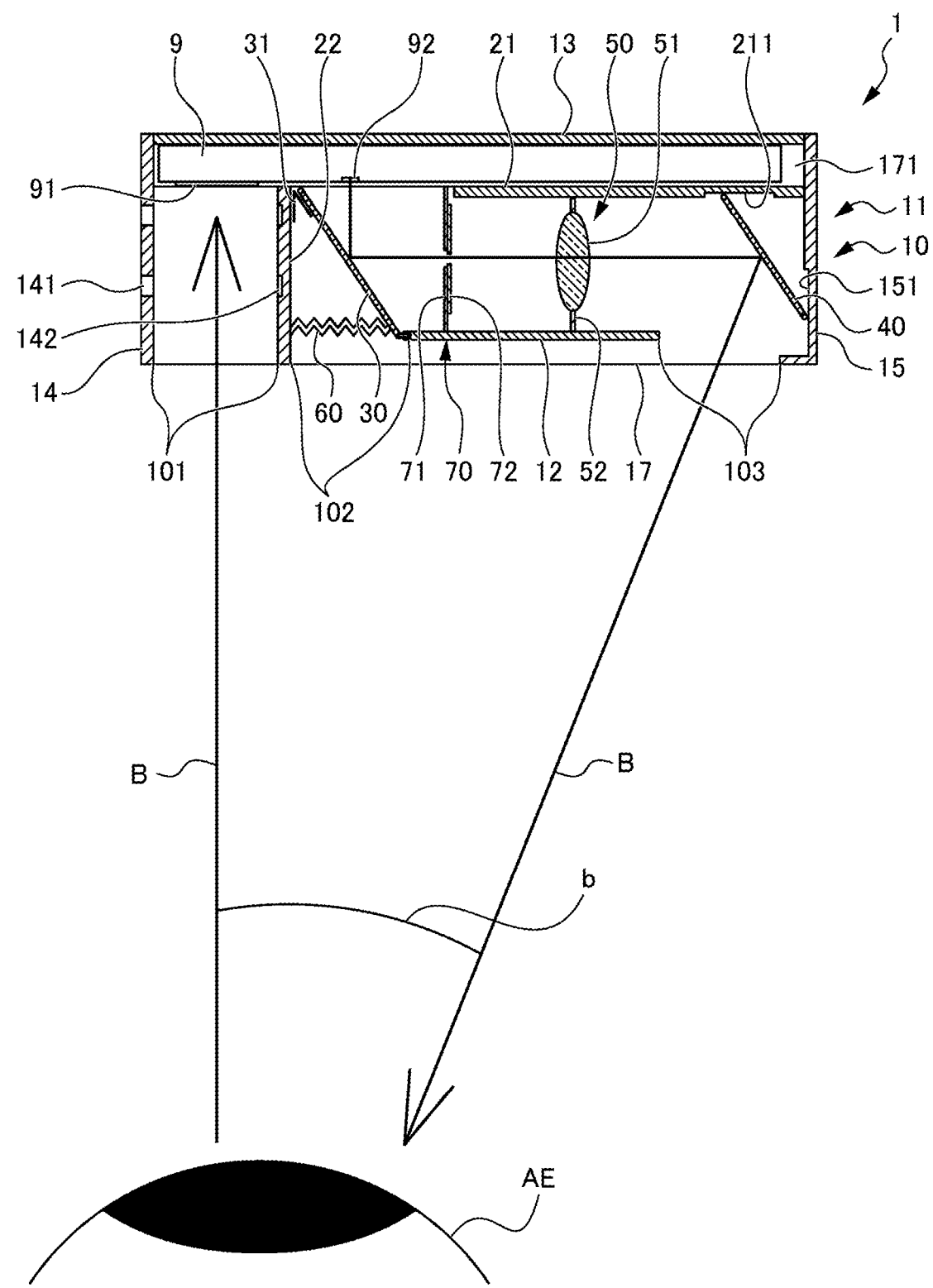
FIG. 2 is a sectional view illustrating a state in which a second optical path B during imaging of an anterior eye AE is formed in the first embodiment of the close-up imaging device according to the present invention.

The close-up imaging device 1 according to the first embodiment of the present invention will now be described with reference to FIG. 1 to FIG. 4. FIG. 1 is a perspective view illustrating the close-up imaging device 1. FIG. 2 is a sectional view illustrating a state in which a second optical path B is formed in the close-up imaging device 1.

In the description below, explanations are given with a direction from a back wall 13 to a front wall 12 described later defined as a forward direction, and a direction opposite thereto defined as a rearward direction. Further, explanations are given with a direction from a right side wall 15 to a left side wall 14 described later defined as a leftward direction, and a direction opposite thereto defined as a rightward direction. Furthermore, explanations are given with a direction from a lower wall 17 to an upper wall 16 described later defined as an upward direction, and a direction opposite thereto defined as a downward direction. In the main drawings, arrows indicating these directions are illustrated.

<Device Configuration>

As illustrated in FIG. 1, the lose-up imaging device 1 is the close-up imaging device imaging 1 fixed and mounted to a smartphone 9 serving as a mobile terminal equipped with a camera lens 91 for imaging and a light source 92, and includes a first optical path forming part, a second optical path forming part, and an optical path switching part, but does not include a configuration for capturing an image, such as a light source and a camera lens. This close-up imaging device 1 is detachably mounted to the smartphone 9. Specifically, the smartphone 9 includes the light source 92 and the camera lens 91 for imaging. The camera lens 91 for imaging is provided to a left end portion of an upper end portion of the smartphone 9, as illustrated in FIG. 2 and the like. Further, the light source 92 is provided to the upper end portion of the smartphone 9, adjacent to the camera lens 91 for imaging, in a portion rightward of the camera lens 91 for imaging.

The close-up imaging device 1 includes a housing 10, a first plate-shaped mirror 30, a second plate-shaped mirror 40, a lens part 50, a bellows part 60, and a slit forming part 70.

(Housing)

As illustrated in FIG. 1, the housing 10 has a hollow side and to rectangular-parallelepiped outer shape. The housing 10 includes an outer wall part 11, a first partition wall part 21, and a second partition wall part 22. The outer wall part 11 constitutes an outer shell of the housing 10.

The outer wall part 11 includes the front wall 12, the back wall 13, the left side wall 14, the right side wall 15, the upper wall 16, and the lower wall 17. A terminal insertion opening 171 (refer to FIG. 2 and the like) is formed in the lower wall 17. The terminal insertion opening 171 is configured by a through hole formed in a rear portion of the lower wall 17, along the back wall 13 from the left side wall 14 to the right side wall 15. The terminal insertion opening 171 is configured so that the upper end portion of the smartphone 9 can be inserted by having a width of the terminal insertion opening 171 in the forward-rearward direction slightly wider than a thickness of the smartphone 9, and a width of the terminal insertion opening 171 in the leftward-rightward direction slightly wider than a width of the smartphone 9.

Lower end portions of the left side wall 14, the back wall 13, and the right side wall 15 extend in the upward direction from a left side, a rear side, and a right, side of the lower wall 17, respectively, and are connected to a left side, a rear side, and a right side of the upper wall 16, respectively. Further, a lower end portion of the front wall 12 extends in the upward direction from a portion slightly rearward of a front side of the lower wall 17, and is connected to a portion slightly rearward of a front side of the upper wall 16.

As illustrated in FIG. 2, the front wall 12 is provided to a central portion of the housing 10, and an opening is formed between a left end portion of the front wall 12 and the left side wall 14 and between a right end portion of the front wall 12 and the right side wall 15, respectively. A width of the opening on the left side in the leftward-rightward direction is about twice a width of the opening on the right side in the same direction. The opening on the left side is divided into two in the leftward-rightward direction by the second partition wall part 22.

The opening on the left side of the opening divided into two has a positional relationship facing the camera lens 91 for imaging of the smartphone 9 in the forward-rearward direction, and constitutes an incoming light opening 101. The opening on the right side of the opening divided into two has a positional relationship facing the light source 92 of the smartphone 9 in the forward-rearward direction, and constitutes a first outgoing light opening 102. Further, the opening between the right end portion of the front wall 12 and the right side wall 15 has a positional relationship facing the second plate-shaped mirror 40 in the forward-rearward direction, and constitutes a second outgoing light opening 103.

A groove (not illustrated) is formed in each of the lower wall 17 portion and the upper wall 16 portion forward of the front wall 12. The grooves (not illustrated) are engageable with, for example, of a filter or the like (not illustrated) that converts white light from the smartphone 9 (not illustrated) into blue light, an end portion thereof protruding in an upward-downward direction, and the filter or the like (not illustrated) can be disposed in the first outgoing light opening 102 and the second outgoing light opening 103 by this engagement.

The left side wall 14 has a rectangular shape, as illustrated in FIG. 1 and the like. In a central part of the left side wall 14 in the forward-rearward direction, filter insertion slits 141, each configured by a through hole, are formed at a predetermined interval. The filter insertion slits 141 each have a rectangular shape, and are formed in positional relationships in which a longitudinal direction thereof is oriented in an upward-downward direction.

The right side wall 15 has a rectangular outer shape similar to the left side wall 14. The filter insertion slits 141 such as formed in the left side wall 14 are not formed in the right side wall 15, but a right wall guide concave part 151 for guiding a right end portion of the second plate-shaped mirror 40 is formed in an inner surface of the right side 15, as illustrated in FIG. 2. The right wall guide concave part 151 extends from an upper end portion to the lower end portion of the right side wall 15 and, as illustrated in FIG. 2 and the like, is formed extending from a position in the vicinity of a front end portion of the right side wall 15, in a rearward direction of the right side wall 15, to a position about one-third of a length in the forward-rearward direction of the right side wall 15.

Figure 4:
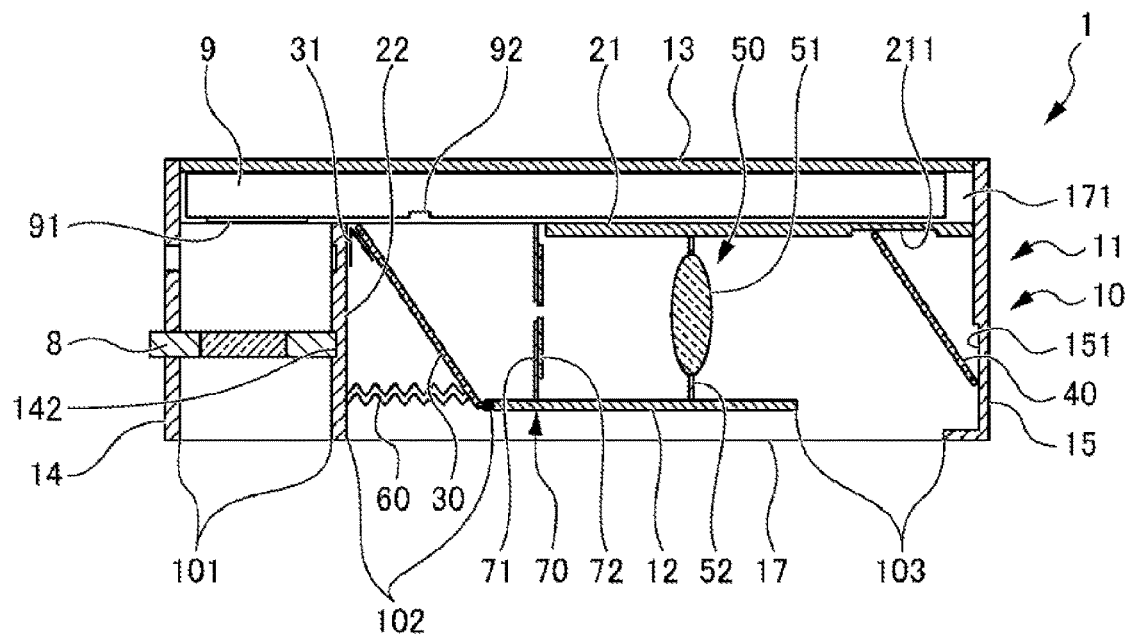
FIG. 4 is a sectional view illustrating mounting of a filter in the first embodiment of the close-up imaging device according to the present invention.
Figure 5:
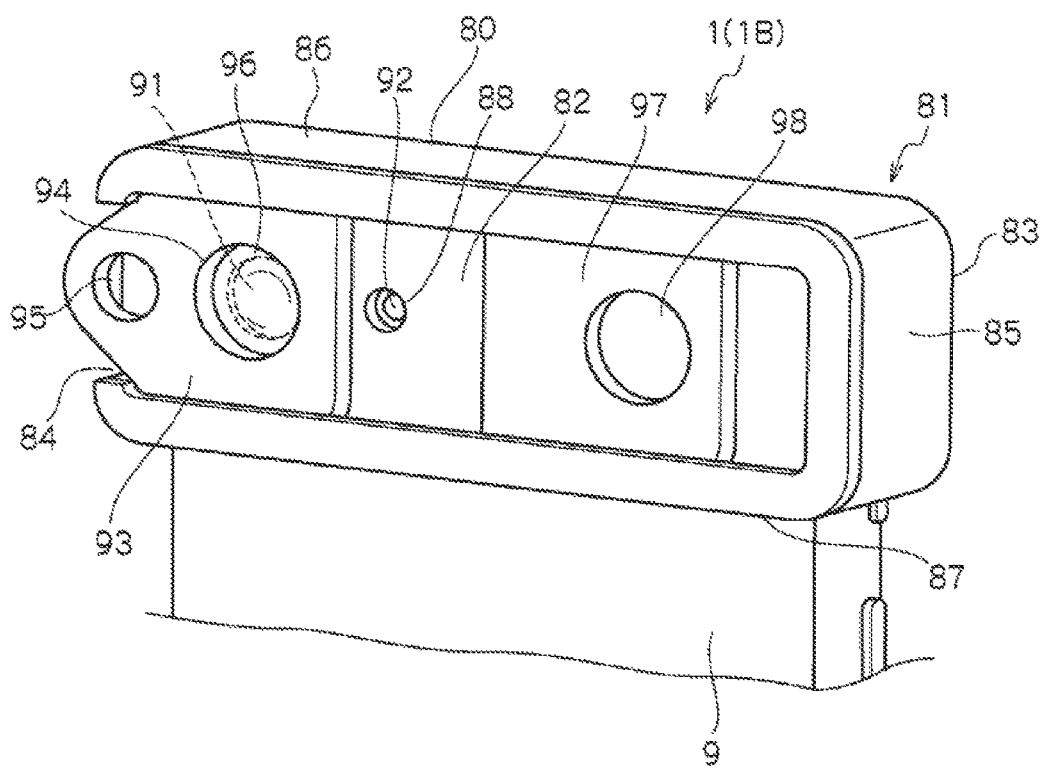
FIG. 5 is a perspective view illustrating a second embodiment of the close-up imaging, device according to the present invention.

The second partition wall part 22 is provided inside the housing 10 facing the left side wall 14, in a position substantially one-sixth of the length of the housing 10 in the leftward-rightward direction, oriented from the left side wall 14 to the right side wall 15. The second partition wall part 22 partitions a space inside the housing 10 in the leftward-rightward direction into a space on an outward path side of the optical path and a space on an inward path side of the optical path. A filter insertion groove 142 is formed on a side surface on a left side of the second partition wall part 22. The filter insertion groove 142 is formed in a position facing the filter insertion slit 141 of the left side wall 14 in the leftward-rightward direction and, as illustrated in FIG. 4, configured so that an end portion on the right side of a plate-shaped filter 8 having a rectangular and inserted from the filter insertion slit 141 is inserted into the filter insertion groove 142 and fixed to the housing 10. FIG. 4 is a sectional view illustrating the filter mounted to the close-up imaging device 1.

Examples of a filter thus inserted include a blue free filter for vital staining examination used when examining keratoconjunctive epithelium disorder and eye injuries with fluorescein, a close-up lens, and the like. The blue free filter for vital staining examination is used by being inserted into the filter insertion slit 141 and the filter insertion groove 142 when a filter that converts white light from the smartphone 9 into blue light is mounted to the second outgoing light opening 103, blue light is emitted onto the eye, the injury on the surface of the eye changes to green, and imaging and observation of the green light are performed through the camera lens 91 for imaging.

(First Plate-Shaped Mirror and Bellows Part)

Further, a left end portion of the bellows part 60 is fixed to the second partition wall part 22. A right end portion of the bellows part 60 is fixed to a front end portion of the first plate-Shaped mirror 30. Convex parts (not illustrated) are provided to the front and portion of the first plate-shaped mirror 30 so as to protrude in the upward-downward direction, and are movable in the leftward-rightward direction by the guidance of grooves (not illustrated) formed in the upper wall 16 and the lower wall 17 in the vicinity of the first outgoing light opening 102 and extending in the leftward-rightward direction. Furthermore, a rear end portion of the first plate-shaped mirror 30 is fixed to one end portion of a hinge 31. The other end portion of the hinge 31 is fixed to a rear end portion of the second partition wall part 22. The first plate-shaped mirror 30 is configured to be pivotable about a rotation axis of the hinge 31 by the pivoting of the hinge 31.

Figure 3:
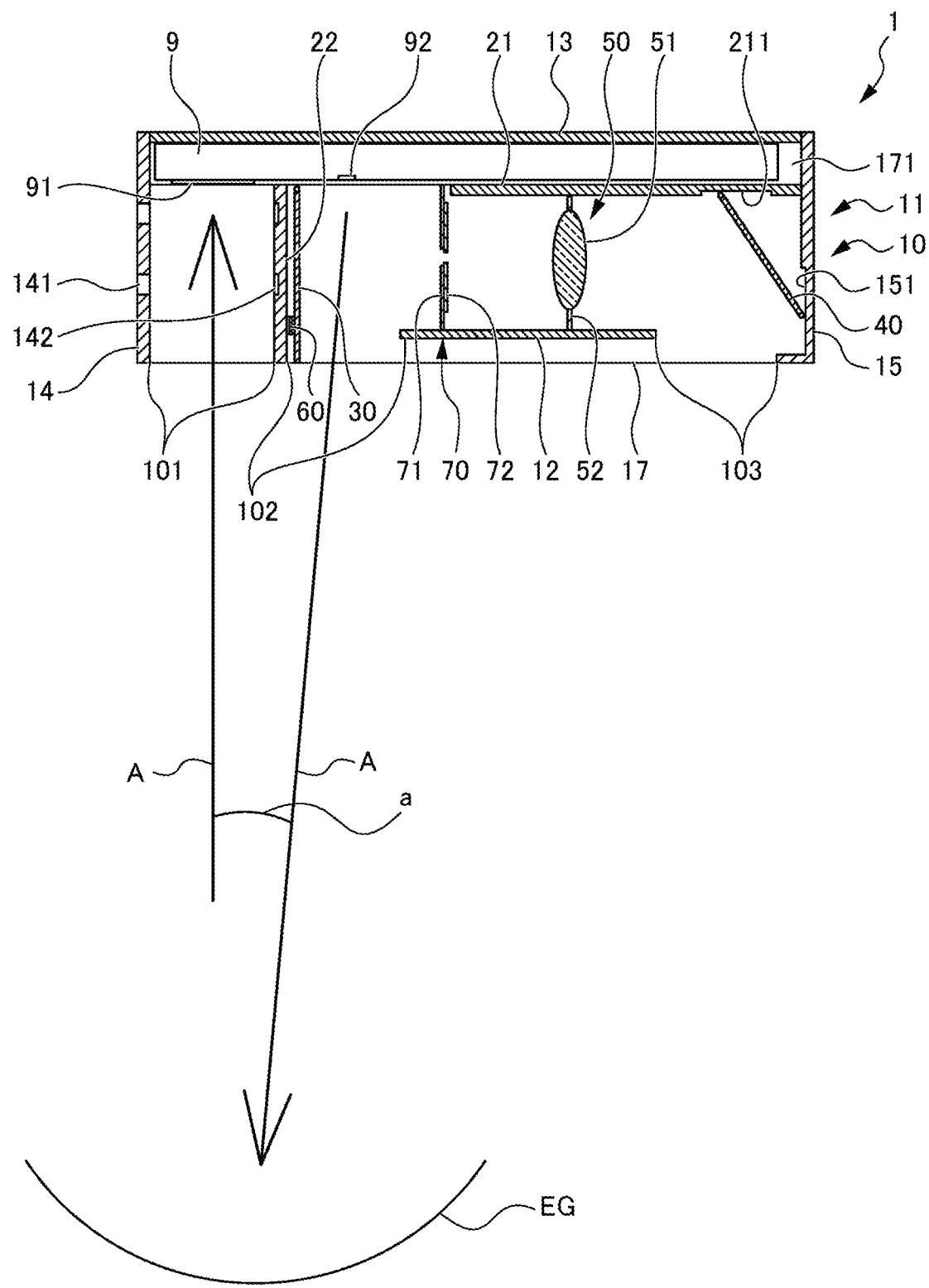
FIG. 3 is a sectional view illustrating a state in which a first optical path A during imaging of an eye ground EG is formed in the first embodiment of the close-up imaging device according to the present invention.

Accordingly, as illustrated in FIG. 2, the front end portion of the first plate-shaped mirror 30 abuts on the left end poetic of the front wall 12, the bellows part 60 is contracted from an extended state, and the first plate-shaped mirror 30 is pivoted about the rotation axis of the hinge 31, thereby causing the convex parts (not illustrated) of the front end portion of the first plate-shaped mirror 30 to move in substantially the leftward direction by the guidance of the grooves (not illustrated) formed in the upper wall 16 and the lower wall 17 in the vicinity of the first outgoing light opening 102 and extending in the leftward-rightward direction. Then, as illustrated in FIG. 3, the first plate-shaped mirror 30 is configured to be in a positional relationship parallel to the second partition wall part 22, thereby causing light from the light source 92 of the smartphone 9 to exit from the first outgoing light opening 102 to outside the close-up imaging device 1 in the forward direction. FIG. 3 is a sectional view illustrating a state in which a first optical path A is formed in the close-up imaging device 1.

The first partition wall part 21 is provided in the lower wall 17 portion forming an edge portion of a front portion of the terminal insertion opening 171. The first partition wall part 21 extends in the upward direction from the lower wall 17 portion to the upper wall 16, and in the leftward direction from the right side wall 15 to the central part of the housing 10 in the same direction. The first partition wall part 21 partitions the space inside the housing 10 in the forward-rearward direction into a space on a front side and a space on a rear side. The upper end portion of the smartphone 9 inserted into the space inside the housing 10 from the terminal insertion opening 171 is disposed in the space on the rear side.

A lens guide groove (not illustrated) extending in the leftward-rightward direction is formed in an inner surface of the first partition wall part 21. Further, a first partition guide concave part 211 for guiding a left end portion of the second plate-shaped mirror 40 is formed in an inner surface of the first partition wall part 21, as illustrated in FIG. 2. The first partition guide concave part 211 extends from an upper end portion to a lower end portion of the first partition wall part 21 and, as illustrated in FIG. 2 and the like, is formed extending from a position of the first partition wall part 21 in the vicinity of the right side wall 15 to a position leftward of a center of the second outgoing light opening 103 of the front wall 12 described later.

(Second Plate-Shaped Mirror)

A Convex part is provided to a left end portion of the second plate-shaped mirror 40 so as protrude in the upward direction, and the convex part protruding in the upward direction protrudes outward of the upper wall 16 to constitute a left side knob 42 (refer to FIG. 1), and is engaged with a groove 162 formed in the upper wall 16 and extending in the leftward-rightward direction at a length of about 3 mm.

The left side knob 42 is configured to move in the leftward-rightward direction by the guidance of the groove 162. The left end portion of the second plate-shaped mirror 40 is configured to move in the leftward-rightward direction by the guidance of the first partition guide concave part 211 formed in the first partition wall part 21 by moving the left side knob 42 along the groove 162.

Further, a convex part is provided to the right end portion of e second plate-shaped mirror 40 so as to protrude in the upward direction, and the convex part protruding in the upward direction protrudes outward of the upper wall 16 to constitute a right side knob 41, and is engaged with a groove 161 formed in the upper wall 5 and extending in the forward rearward direction. The right side knob 41 is configured to move in the forward-rearward direction by the guidance of the groove 161. The right end portion of the second plate-shaped mirror 40 is movable in the forward-rearward direction by the guidance of the right wall guide concave pan 151 formed in the right side wall 15 by moving the right side knob 41 along the groove 161.

(Lens Part)

The lens part 50 is provided so as to be disposed inside the housing 11, in the second optical path thrilling part that forms the second optical path B. Specifically, the lens part 50 is provided so as to be disposed inside the housing 10, in a position between the first partition wall part 21 and the front wall 12. The lens part 50 includes a convex lens 51 (plus lens) and a convex lens folder 52 that holds the convex lens 51. Convex parts (not illustrated) are provided to a front end portion and a rear end portion of the convex lens folder 52 so as to protrude in the forward-rearward direction, and are movable in the leftward-rightward direction by the guidance of grooves (not illustrated) formed in the inner surface of the first partition wall pan 21 and an inner surface of the front wall 12. A convex part protruding in the upward direction is provided to an upper end portion of the convex lens folder 52 and protrudes outward of the upper wall 16 to constitute a lens part knob 53. The lens part knob 53 is configured to engage with a groove 163 formed in the upper wall 16 and extending in the leftward-rightward direction, and move along the groove 163, thereby causing the lens part 50 to move in the leftward-rightward direction by the guidance of the groove 163.

(Slit Forming Part)

The slit forming part 70 is provided so as to be disposed inside the housing 10, in the second optical path forming part that forms the second optical path B. Specifically, the slit forming part 70 is provided so as to be disposed inside the housing 10, in a position between a front surface of the smartphone 9 in the vicinity of a left end portion of the first partition wall part 21 and the front wall 12.

The slit forming part 70 includes a slit plate 71 and a movable plate 72. As illustrated in FIG. 2, the slit plate 71 is provided so as to partition the second optical path B inside the housing 10 into a left side and a right side, and a slit extending in the upward-downward direction is formed in a central part in the forward-rearward direction. The movable plate 72 is configured by a pair of plates movable in the forward-rearward direction, and is coupled to a rotary knob 721. The movable plates 72 are configured to approach each other or separate from each other by rotating the rotary knob 721.

(First Optical Path Forming Part and Second Optical Path Forming Part)

The second partition wall part 22 and the left end portion of the front wall 12 constitute the first optical path forming part that forms the first optical path A. The slit forming part 70, the lens part 50, the first plate-shaped mirror 30, the second plate-shaped mirror 40, the inner surface and the right end portion of the front wall 12, and a front surface of the first partition wall part 21 constitute the second optical path forming part that forms the second optical path B. Further, the bellows part 60 and the first plate-shaped mirror 30 constitute a reflecting member and an optical path switching part that switch between formation of the first optical path A and formation of the second optical path B by the light from the light source 92. Furthermore, the lens part 50 constitutes a focus adjusting part for focusing the light from the light source 92 on the eye serving as an irradiated object irradiated with light. In addition, the second plate-shaped mirror 40 constitutes an irradiation position adjusting part capable of adjusting an irradiation position on the eye serving as the irradiated object irradiated with light.

<Imaging of Anterior Eye and Imaging of Eye Ground>

Imaging of an anterior eye AE and imaging of an eye ground EG using the close-up imaging device 1 according to a configuration such as described above will now be described.

(Imaging of Eye Ground)

First, imaging of the eye ground EG will be described. When an image of the eye ground EG is captured, the front end portion of the first plate-shaped mirror 30, as illustrated in FIG. 2, comes into contact with the left end portion of the front wall 12 and the bellows part 60 is contracted from an extended state, thereby causing the first outgoing light opening 102 to start to open.

Then, with further contraction of the bellows part 60, as illustrated in FIG. 3, the first plate-shaped mirror 30 is in a positional relationship parallel to the second partition wall part 22, the first outgoing light opening 102 becomes completely open, and light is irradiated from the light source 92 with a distance from the camera lens 91 for imaging to the eye at about 4 cm, thereby forming the first optical path A. That is, light is irradiated from the light source 92, through the first outgoing light opening 102, from substantially a front face of the eye onto the eye ground EG and, of the light reflected by the eye ground EG, the light oriented toward the camera lens 91 for imaging passes enters the camera lens 91 for imaging through the incoming light opening 101. The light that entered the camera lens 91 for imaging, by execution of application software in the smartphone 9, is stored in a storage medium included in the smartphone 9, and imaging is performed. An angle α connecting the light source 92, the eye ground EG, and the camera lens 91 for imaging in the first optical path A is 5° to 15°, inclusive.

(Imaging of Eye Ground)

Next, imaging of the anterior eye AE will be described. When an image of the anterior eye AE is captured, the bellows part 60 is expanded from a state in which the first plate-shaped mirror 30 is in the positional relationship parallel to the second partition wall part 22, thereby causing the first outgoing light opening 102 to start to close. Then, with further expansion of the bellows part 60, the first outgoing light opening 102 is closed, as illustrated in FIG. 2. In this state, light is irradiated from the light source 92 with the distance from the camera lens 91 for imaging to the eye at about 4 cm, thereby forming the second optical path B. That is, light is irradiated from the light source 92, through the second outgoing light opening 103, from a diagonal relative to the front face of the eye onto the anterior eye AE and, of the light reflected by the anterior eye AE, the light oriented toward the camera lens 91 for imaging enters the camera lens 91 for imaging through the incoming light opening 101. An angle b connecting the second outgoing light opening the anterior eye AE, and the camera lens 91 for imaging in the second optical path B is 30° to 60°, inclusive.

At this time, a width of the slit in the slit forming part 70 is adjusted to set a width of the linear light irradiated onto the anterior eye AE to a desired width by rotating the rotary knob 721 (refer to FIG. 1). Further, the lens part knob 53 is appropriately moved in the leftward-rightward direction to focus the linear light irradiated onto the anterior eye AE. Furthermore, an angle of the second plate-shaped mirror 40 is changed to adjust the irradiation position of the linear light on the anterior eye AE by moving the left side knob 42 and the right side knob 41 along the groove 161. Then, by these adjustments, the light irradiated from the light source 92 onto the anterior eye AE through the second, optical path B and reflected by the anterior eye AE becomes optimal light, enters the camera lens 91 for imaging and, by execution of application software in the smartphone 9, is stored in the storage medium included in the smartphone 9, and imaging is performed.

<Effects>

According to the close-up imaging device 1 of the embodiment having the above-described configuration, the following effects can be obtained. As mentioned above, the close-up imaging device 1 mounted to the smartphone 9 serving as a mobile terminal equipped with the light source 92 and the camera lens 91 for imaging includes the first optical path forming part that forms the first optical path A by the light from the light source 92, the second optical path forming part that forms the second optical path B, different from the first optical path A, by the light from the light source 92, and the optical path switching part that switches between formation of the first optical path A and formation of the second optical path B by the light from the light source 92.

With this configuration, it is possible to easily mount the close-up imaging device 1 as an attachment externally attached to the smartphone 9 widely used throughout the world and capture all still images and moving images obtained in an ophthalmic examination of a patient, that is, still images and moving images of both the anterior eye AE and the eye ground EG. Furthermore, the close-up imaging device 1 is significantly inexpensive compared to a slit lamp biomicroscope or a handheld slit lamp biomicroscope, making it easy to prepare a plurality of devices and, by using a device prepared for animals separately from human clinical use, it is possible to capture still images and moving images of the eyes of experimental animals (animal models), companion animals such as pets, and reared animals in zoos and acquire ophthalmic findings of the above-described animals as well.

Further, clinical use is possible. Specifically, in an ophthalmic examination, the examination is performed with the patient fixed onto a provided stand. Therefore, medical examinations for children and the bedridden elderly require expert skills. However, in the close-up imaging device 1 according to the present embodiment, the element of "recording" is added to the portable medical instrument, and recorded still images and moving images can be shared among medical personnel. The shared data can be expected to be utilized in remote medical care in rural areas and support for developing countries, and can be further expected to improve a diagnostic accuracy of ophthalmologists by being analyzed by artificial intelligence (AI) big data. Then, finally, the close-up imaging device 1 is used as a self-diagnostic tool by all smartphone users, making possible to further develop the ophthalmic examination itself.

Further, the close-up imaging device 1 according to the present embodiment can be utilized for research. Specifically, the findings of the eyes of research animals to date could not be substantially recorded due to various technical problems (skillful technique is required, the target animal must be killed during imaging, imaging equipment is expensive, and the like). However, by using the close-up imaging device 1 according to the present embodiment, it is possible to easily obtain eye findings of research animals, and thus expect birth of a new phenotype the research field of the eye.

Further, the optical path switching part includes the first plate-shaped mirror 30 serving as a reflecting member capable of reflecting the light from the light source 92, the first optical path A is formed by light from the light source 92 not being reflected by the first plate-shaped mirror 30, and the second optical path B is formed by light from the light source 92 being reflected by the first plate-shaped mirror 30. With this configuration, by driving the first plate-shaped mirror 30, it is possible to easily switch between the first optical path A and the second optical path B.

Further, the second optical path B is provided with the lens part 50 serving as a focus adjusting, part for focusing the light from the light source 92 from the second optical path B on the irradiated object irradiated with light. With this configuration, by moving the convex lens 51 of the lens part 50, it is possible to easily focus the light on the eye ground EG and the anterior eye. AE serving as the irradiated object irradiated with light.

Further, the second optical path B is provided with the second plate-shaped mirror 40 serving as an irradiation position adjusting part capable of adjusting an irradiation position on the eye (eye ground EG and anterior eye AE) serving as the irradiated object irradiated with light. With this configuration, it is possible to change the irradiation position of the light on the eye without moving the smartphone 9 and the housing 10 relative to the eye, and irradiate light onto the eye to be observed at an appropriate angle and light quantity.

Further, the second optical path B is provided with the slit forming part 70 that forms the light from the light source 92 into linear light. With this configuration, it is possible to form the light from the light source 92 of the smartphone 9 into linear light, irradiate the linear light onto the eye, and irradiate the light onto the eye to be observed at an appropriate angle and light quantity.

<Applications and Modifications>

The present invention is not limited to the embodiment mentioned above, and can be modified within the technical scope described in the claims. For example, while the smartphone 9 is used, the present embodiment is not limited to the smartphone 9. The mounted object to which the close-up imaging device is mounted may be any mobile terminal equipped with a light source and a camera lens for imaging, such as, for example, a tablet terminal.

Further, the configurations of the first optical path forming part, the second optical path forming part, the optical path switching part, the reflecting member, the focus adjusting part, the irradiation position adjusting part, the slit forming part, and the like are not limited to the second partition wall part 22 and the left end portion of the front wall 12, the slit forming part 70, the lens part 50, the first plate-shaped mirror 30, the second plate-shaped mirror 40, the inner surface and the right end portion of the front wall 12, and the front surface of the first partition wall part 21 in the present embodiment.

Further, the close-up imaging device 1 according to the present embodiment is conceivably used in an ophthalmic examination, but is not limited to being used in an ophthalmic examination. For example, the close-up imaging device 1 may be used not only in an ophthalmic outpatient clinic, but also in a place other than an ophthalmic clinic, such as a medical examination place, a long-term care health facility for the elderly, an ambulance, and a science, health, or medical school class. In addition, the close-up imaging device 1 can be used in animal related facilities such as an animal hospital, a zoo health center, and a research institute, as well.

Second Embodiment

A close-up imaging device 1B according to a second embodiment of the present invention is, as illustrated in FIG. 5 to FIG. 15, the close-up imaging device 18 detachably mounted to a mobile terminal (smartphone 9) equipped with the light source 92 and the camera lens 91 for imaging, and includes a color filter member 97 detachably provided above the light source 92, and a convex lens member 93 detachably provided above the camera lens 91. With this close-up imaging device 1B, imaging of the anterior eye is performed by removing the color filter member 97 and attaching the convex lens member 93, and observation of an injury of the anterior eye is performed by attaching the color filter member 97 and the convex lens member 93. This way, imaging of the anterior eye and observation of an injury can be performed by attaching and detaching the color filter member 97 with the convex lens member 93 attached. It should be noted that the close-up imaging device 18 may further detachably include a slit light forming member 61 (FIG. 8 to FIG. 10) that forms light from the light source 92 into slit light by a cylindrical lens 62, and a tubular member 180 (FIG. 11 to FIG. 13) including, a convex lens 183 at a tip end thereof.

<Device Configuration>

In the device configuration of the second embodiment, the outer wall part 11, the front wall 12, the back wall 13, the left side wall 14, the right side wall 15, the upper wall 16, and the lower wall 17 in the first embodiment are respectively expressed as an outer wall part 81, a front wall 82, a back wall 83, a left side wall 84, a right side wall 85, an upper wall 86, and a lower wall 87 in the second embodiment. Accordingly, these components are the same as those already described in the first embodiment, and explanations thereof are omitted here unless otherwise specified. Further, the directions are also the same, and explanations are given with a direction from the back wall 83 to the front wall 82 defined as a forward direction, and a direction opposite thereto defined as a rearward direction. Furthermore, explanations are given with a direction from the right side wall 85 to the left side wall 84 defined as a leftward direction, and a direction opposite thereto defined as a rightward direction. In addition, explanations are given with a direction from the lower wall 87 to the upper wall 86 defined as an upward direction, and a direction opposite thereto defined as a downward direction.

(Housing)

Figure 7:
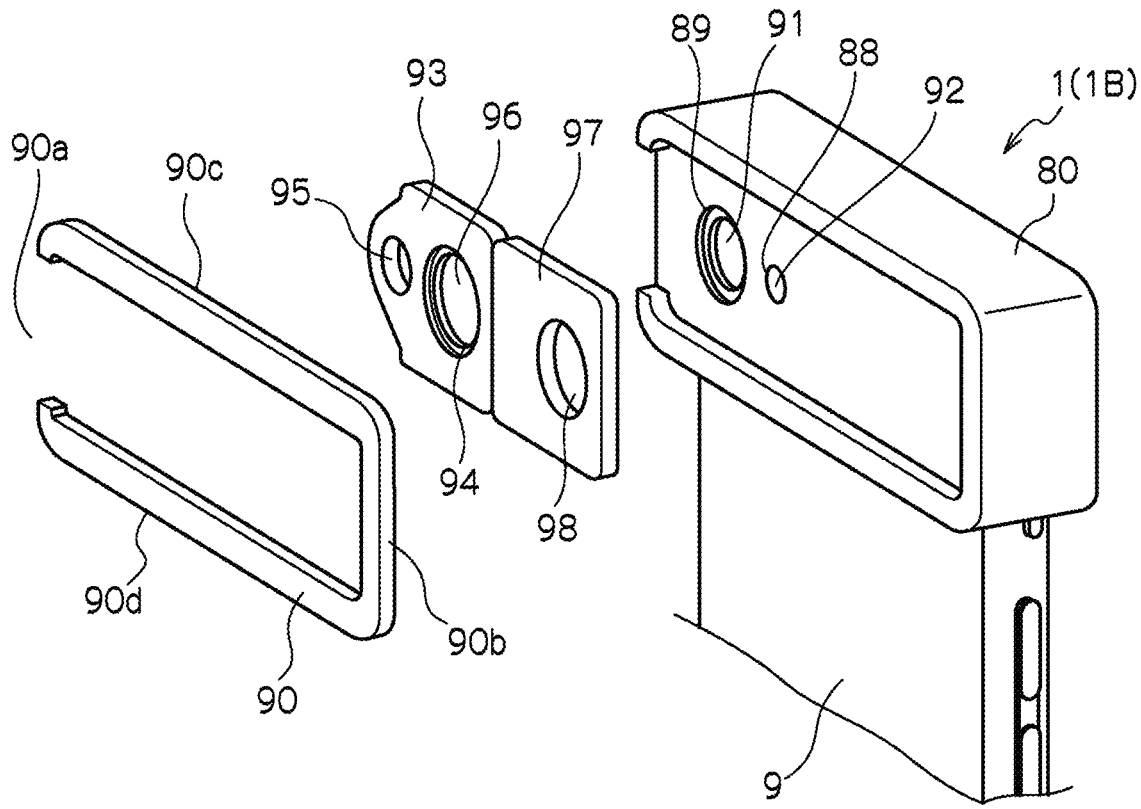
FIG. 7 is an exploded configuration view of the second embodiment of the close-up imaging device illustrated in FIG. 5.

A housing 80 has a hollow inside and a rectangular-parallelepiped outer shape. The housing 80, as illustrated in FIG. 7, is configured by the outer wall part 81 and a front surface plate 90. The outer wall part 81 includes the front wall 82, the back wall 83, the left side wall 84, the right side wall 85, the upper wall 86, and the lower Wall 87. An opening (not illustrated) in which the smartphone 9 is inserted is formed in the lower wall 87. The opening is configured by a through hole formed from the left side wall 84 side to the right side wall 85 side. The opening is configured so that the upper end portion of the smartphone 9 is inserted by having an opening width in the forward-rearward direction slightly wider than the thickness of the smartphone 9, and an opening width in the leftward-rightward direction slightly wider than the width of the smartphone 9.

The front wall 82 includes a peripheral edge portion in which an upper edge, a lower edge, and a right edge are convex in a frame form in the forward direction. The front surface plate 90 having a width wider than a width of the peripheral edge portion is mounted to the peripheral edge portion. The front surface plate 90 is a frame-like body with a central part opened, configured by an opened left edge portion 90a, a right edge portion 90b, an upper edge portion 90c, and a lower edge portion 90d. The width of the front surface plate 90 is wider than that of the peripheral edge portion of the front wall 82. Therefore, the front surface plate 90 is provided so as to project inside the peripheral edge portion. The projecting portion functions as upper and lower rails, and the plate-shaped color filter member 97 and the plate-shaped convex lens member 93 are slidably fitted into the upper and lower rails. The gap between the front wall 82 and the projecting portion of the front surface plate 90 is formed slightly larger than thicknesses of the plate-shaped color filter member 97 and the plate-shaped convex lens member 93, at slidable dimensions. It should be noted that, the opening is the left edge portion 90a in the example in FIG. 5, but may be the right edge portion 90b.

The front wall 82 is provided with two holes. One hole 89 is provided in a position corresponding to the camera lens 91 for imaging of the smartphone 9, and the other hole 88 is provided in a position corresponding to the light source 92 of the smartphone 9. With these two holes 88, 89, it is possible to emit light from the light source 92 of the smartphone 9 in the forward direction, and receive the inward light by the camera lens 91 for imaging of the smartphone 9 to capture an image of the anterior eye or the eye ground.

(Color Filter Member)

The color filter member 97 is detachably provided above the light source 92. This color filter member 97 is a plate-shaped member, and attached and detached above the light source 92 by being slid. This color filter member 97 is preferably a blue filter that turns white light emitted from the light source 92 of the smartphone 9 into blue light. For example, a blue filter, that converts white light into blue light having a wavelength of 488 nm is preferred. The blue filter adopted may be a colored acrylic resin.

A hole 98 provided in the color filter member 97 is a hole in which a finger is hooked when sliding the color filter member 97. This may not necessarily be a hole as long as a finger can be hooked onto it to slide the color filter member 97, and may be a protrusion.

The light source 92 can be covered and uncovered by sliding the color filter member 97 in the leftward-rightward direction. That is, the color fiber member 97 is attached and detached from above the light source 92 or the convex lens member 93 is attached and detached from above the camera lens 91 for imaging by sliding the color filter member 97 and the convex lens member 93. In the present invention, observation and imaging of the anterior eye can be performed by removing the color filter member 97 from the light source 92. Further, observation and imaging of an injury of the anterior eye can be performed by covering the light source 92 with the color filter member 97. For example, fluorescein eyedrops are administered to the eye and a blue free filter for vital staining examination is adopted as the color filter member 97, making it possible to emit blue light onto the eye to change the injury on the surface of the eye to green, and observe and capture an image of the green light through the camera lens 91 for imaging. As a result, it is easier to examine keratoconjunctive epithelium disorder and eye injuries, making it possible to observe and capture images of injuries and the like of the anterior eye.

(Convex Lens Member)

The convex lens member 93 is detachably provided above the camera lens. This convex lens member 93 is a plate-shaped member, and attached and detached above the camera lens 91 for imaging by being slid. This convex lens member 93 includes a convex lens 96 that condenses light on the camera lens 91 for imaging of the smartphone 9. The convex lens 96 is selected as desired in consideration of the focal length. The convex lens 96 is mounted in a hole 94 provided in the convex lens member 93. With the convex lens 96, it is possible to adjust the focus on the eye of a mouse or a human, correct blurring of an image, and perform clear observation and imaging.

A hole 95 provided in the convex lens member 93 is a hole in which a finger is hooked when sliding the convex lens member 93 and, with the convex lens member 93 slid to dispose the hole 95 above the light source 92, acts to improve a directivity of the light emitted from the light source 92 as well.

Figure 6A:
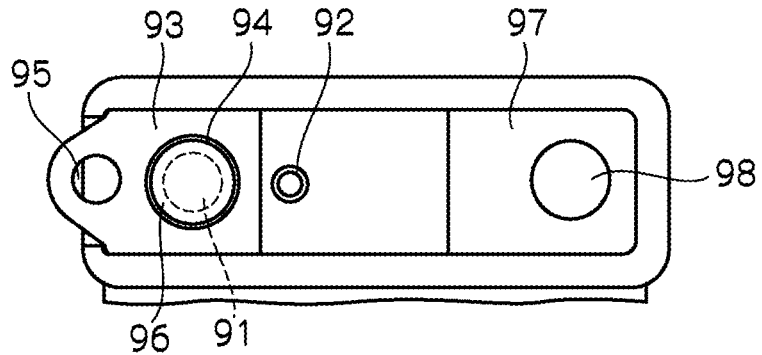
FIGS. 6A to 6C are explanatory views illustrating form examples in which a convex lens member and a color filter member are slid.
Figure 6B:
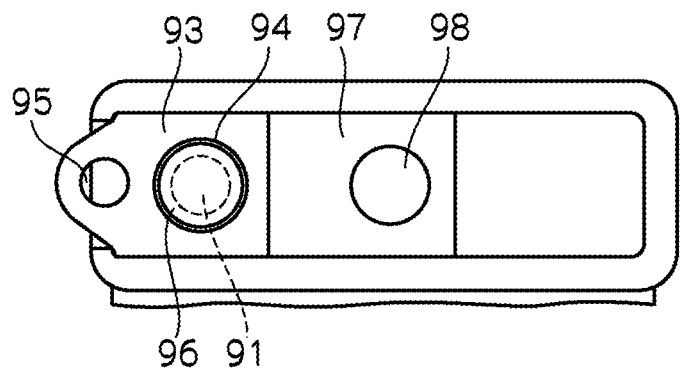
Figure 6C:
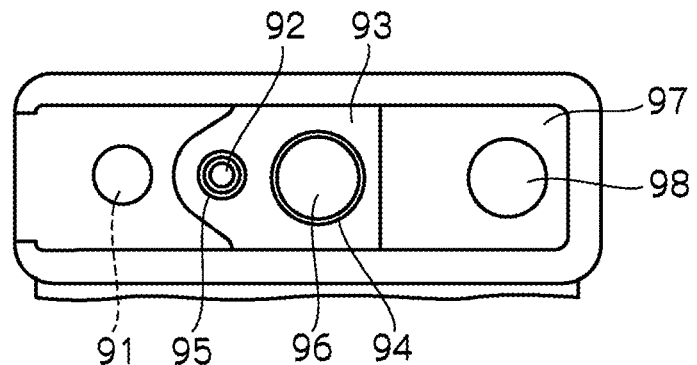

FIGS. 6A to 6C illustrate forms in which the color filter member 97 and the convex lens member 93 are slid. FIG. 6A is a form in which the convex lens 96 of the convex lens member 93 is mounted above the camera lens 91 for imaging, and the color filter member 97 is slid in the leftward direction and removed from above the light source 92. FIG. 6B is a form in which the convex lens 96 of the convex lens member 93 is mounted above the camera lens 91 for imaging, and the color filter member 97 is slid in the rightward direction and mounted above the light source 92. FIG. 6C is a form in which the color filter member 97 is slid in the leftward direction and removed from above the light source 92, and the convex lens 96 of the convex lens member 93 is removed from above the camera lens 91 for imaging. It should be noted that, in this FIG. 6C, the hole 95 of the convex lens member 93 is disposed above the light source 92, and thus the directivity of the light emitted from the light source 92 can be improved.

(Slit Light Forming Member)

Figure 8:
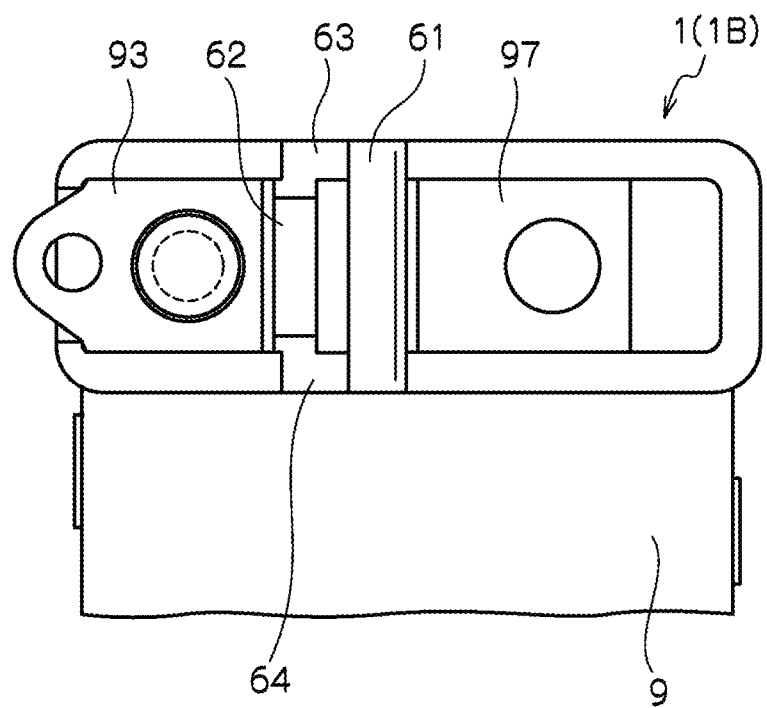
FIG. 8 is a front view illustrating a firm in which a slit member is attached.
Figure 9:
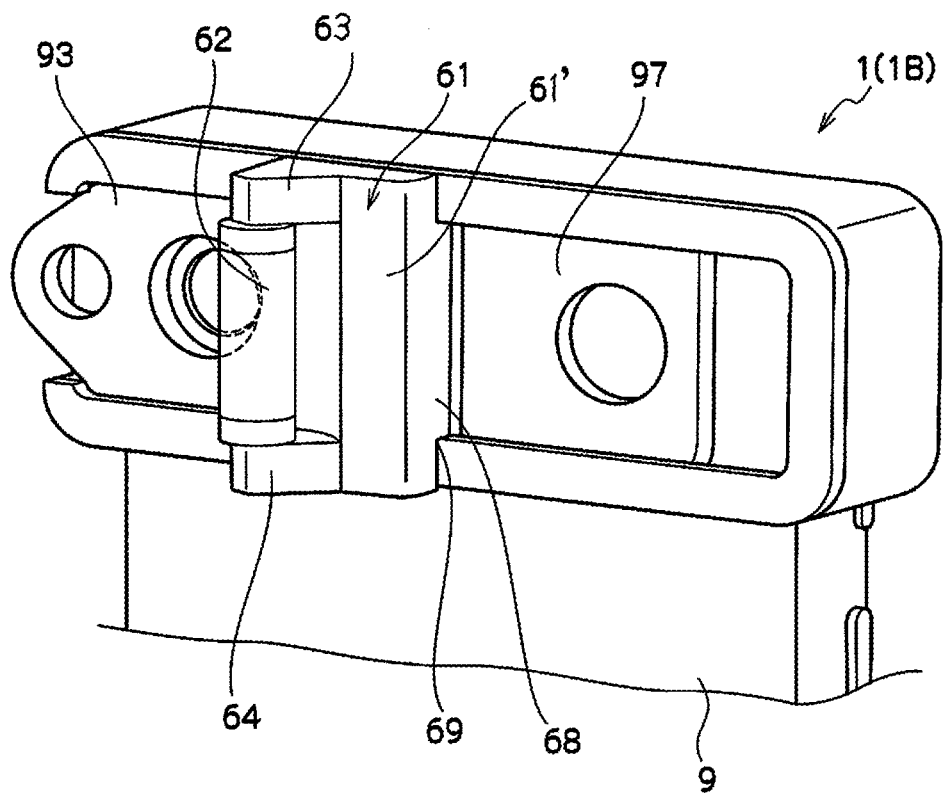
FIG. 9 is a perspective view of the form illustrated in FIG. 8.
Figure 10:
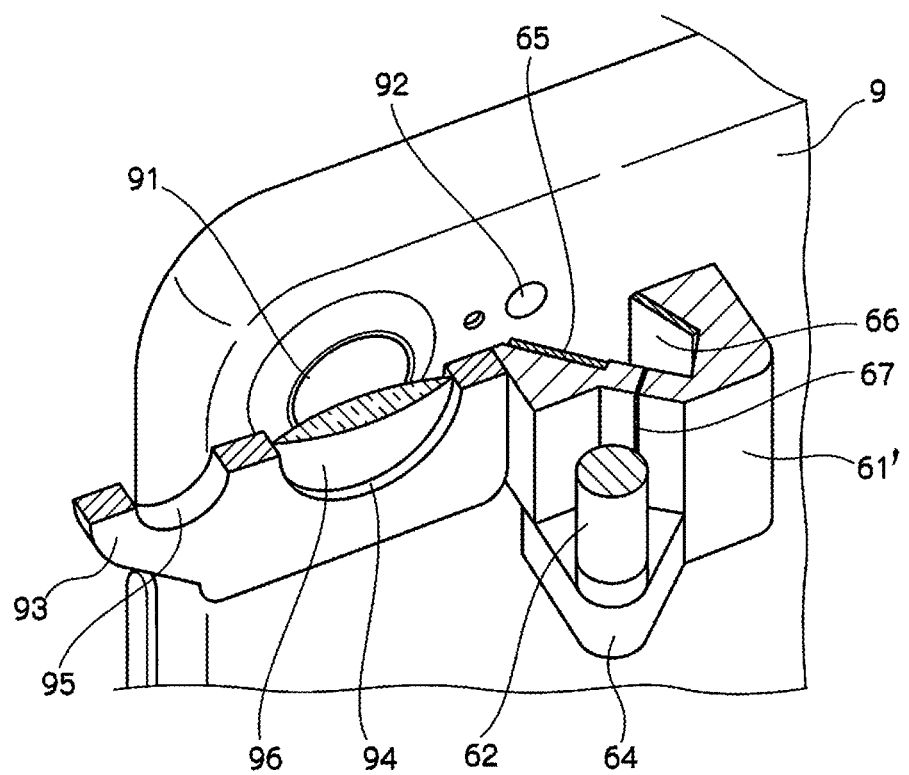
FIG. 10 is an explanatory view of the form illustrated in FIG. 8.
Figure 11:
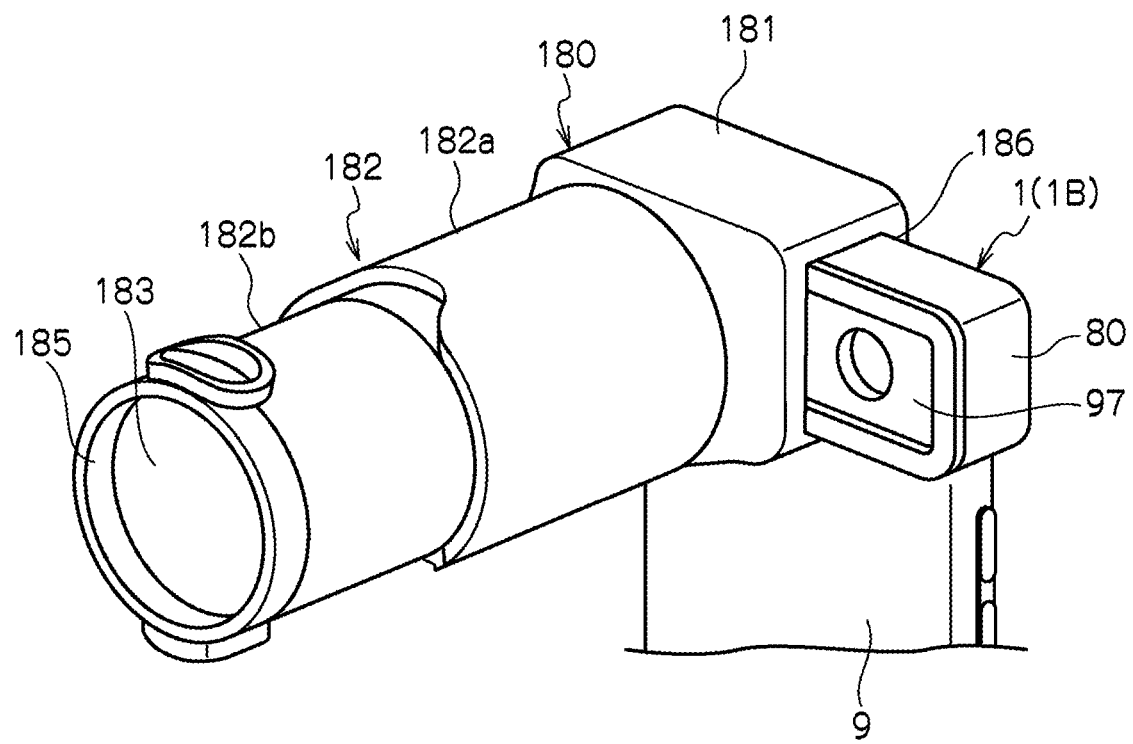
FIG. 11 is a perspective view illustrating a form including a tubular lens member
Figure 12:
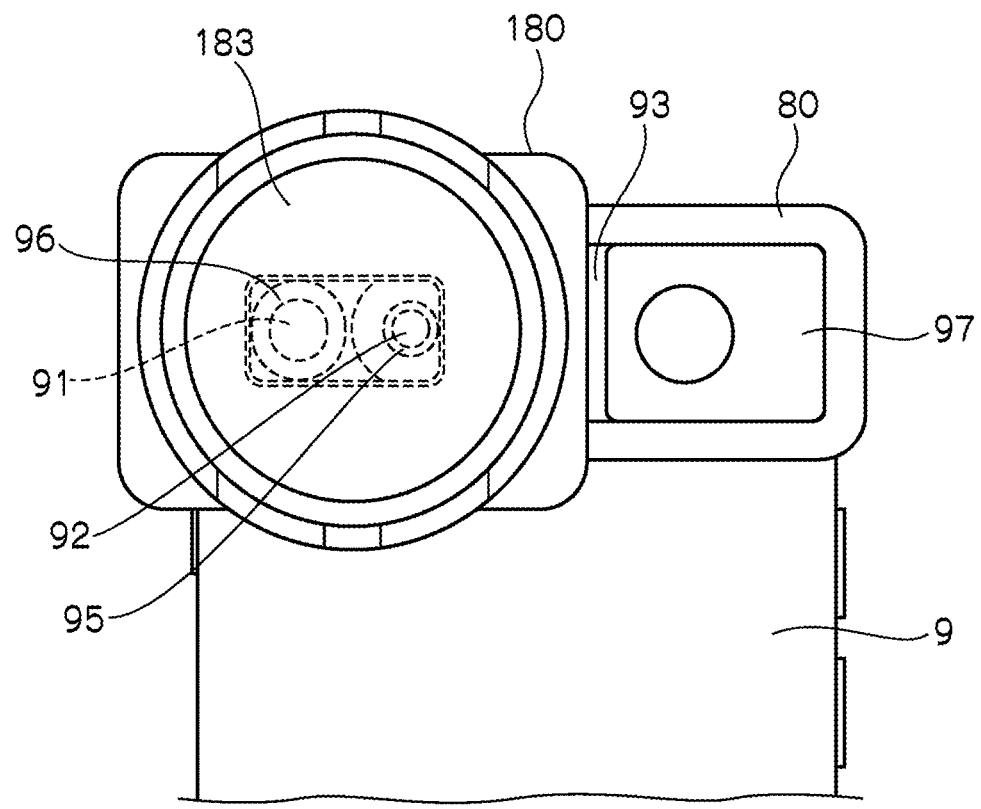
FIG. 12 is a front view of the form illustrated in FIG. 11.

The slit light forming member 61, as illustrated in FIG. 8 to FIG. 10, is a member that forms the light from the light source 92 into slit light by the cylindrical lens 62. The attaching/detaching means of the slit light forming member 61 is not particularly limited, but preferably the slit light forming member 61 is detachably provided on the upper and lower rails on which the color filter member 97 and the convex lens member 93 are slid. With such a slit light forming member 61, observation and imaging of an internal structure of the anterior eye can be performed in more detail by the slit light formed by the cylindrical lens 62.

The slit light forming member 61, as illustrated in FIG. 8, includes an upper holding member 63 that holds the cylindrical lens 62 from above, and a lower holding member 64 that holds the cylindrical lens 62 from below. FIG. 9 is an example in which the slit light forming member 61 is mounted to a front surface of the housing 80 together with the color filter member 97 and the convex lens member 93, and includes a mounting part 68 and a step part 69 attached to the upper and lower rails. Reference numeral 61' denotes a main body part including a first reflecting mirror 65 and a second reflecting mirror 66 described later.

The main body part 61' of the slit light forming member 61, as illustrated in FIG. 10, includes the first reflecting mirror 65 that reflects the light from the light source 92, the second reflecting mirror 66 that reflects the light reflected by the first reflecting mirror 65, and a slit part 67 for allowing the light reflected by the second reflecting mirror 66 to pass therethrough. The light that passes through the slit part 67 becomes slit light by the cylindrical lens 62. This slit light reaches the eye, making it possible to observe and capture an image of the internal structure of the anterior eye in more detail.

This cylindrical lens 62 is not particularly limited, but can be selected and adopted from various cylindrical lenses 62. The slit part 67 is preferably a narrow slit having a minimum width of approximately 1 mm. As the range, the slit part 67 is preferably formed with a width of about 1 mm to 1.5 mm.

(Tubular Member)

The tubular member 180, as illustrated in FIG. 12 to FIG. 15, is a member including a convex lens 183 at a tip end thereof. This tubular member 180 is also detachably provided to the smartphone 9. The tubular member 180 is configured by at least a mounting part 181 for mounting to the smartphone 9, a tube part 182 (182a, 182b), the convex lens 183, an opening 184, a convex lens holding part 185, and a mounting part 186. With such a tubular member 180, the focal length from the eye ground can be adjusted to and maintained in an appropriate state. As a result, observation and imaging of the eye ground can be performed.

In the opening 184 of this tubular member 180, a color filter (orange) 4 and a polarizing filter (horizontally polarized light) 3 are disposed in that order in an optical path position of the outward light emitted from the light source 92. Further, a polarizing filter (vertically polarized light) 2 is provided in an optical path position immediately before the inward light reflected by the eye ground reaches the camera lens 91 for imaging. Each of the polarizing filters 2, 3 may be either vertically polarized light or horizontally polarized light as long as one is vertically polarized light and the other is horizontally polarized light. By thus changing the angles of the light in the outward path and the inward path, it is possible to prevent the outward light and the inward light from interfering with each other inside the tubular member 180. As a result, observation and imaging of the eye ground by the inward light can be clearly performed.

The orange color filter 4 is a filter for converting the light of the outward path into light that easily reaches the retina to the extent possible.

Figure 13:
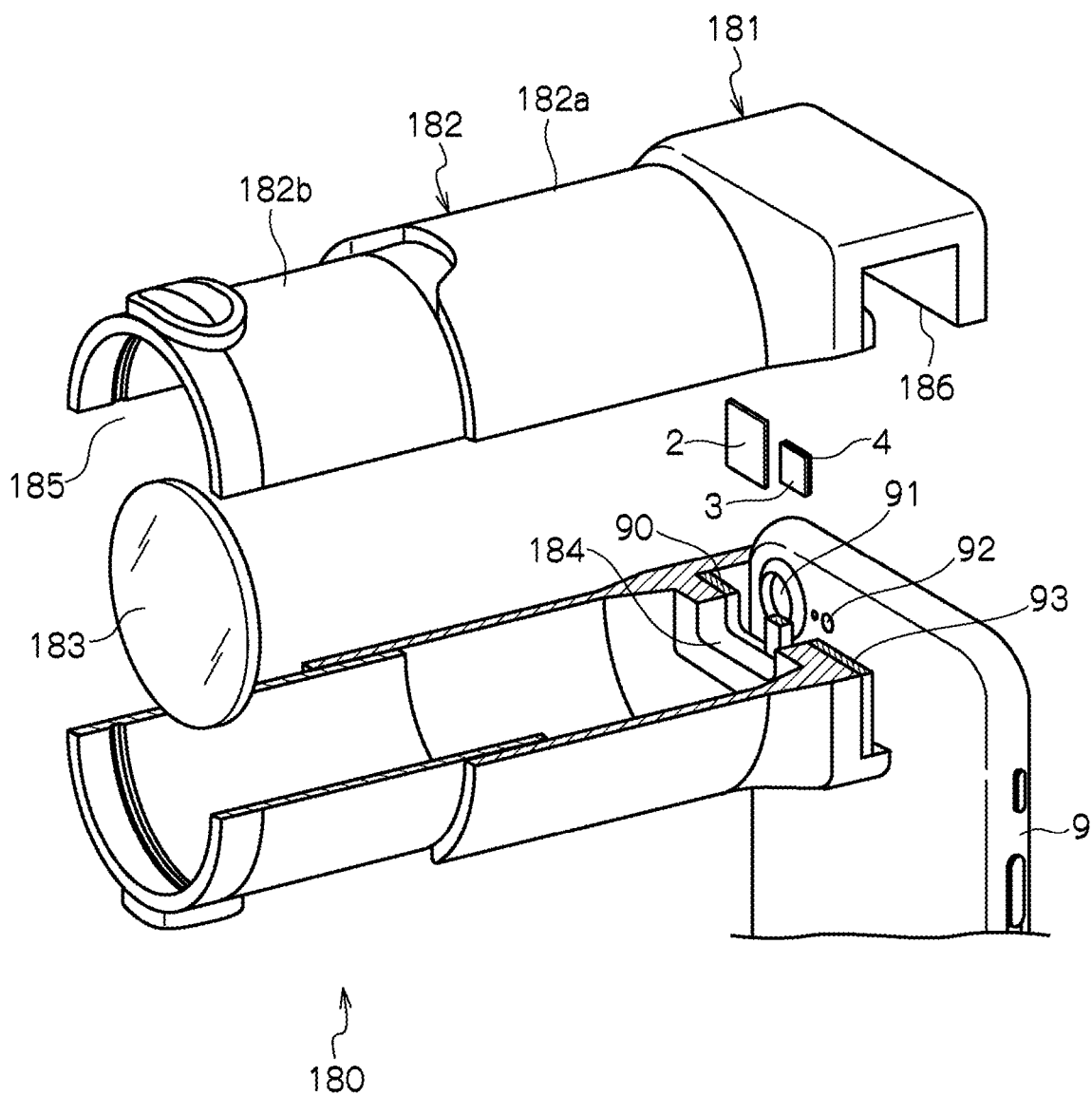
FIG. 13 is an exploded configuration view of the form illustrated in FIG. 11.

As illustrated in FIG. 13, the mounting part 186 for mounting to the smartphone 9 is configured to be mountable by sliding on the smartphone 9 from the left side wall 84 side. In the tubular member 180 after mounting, the color filter (orange) 4 and the polarizing filter 3 are provided forward of the light source 92, and the other polarizing filter 2 is provided forward of the camera lens 91 for imaging. While configured by combining the two tube parts 182a, 182b in the illustrated example, the tube part 182 is not particularly limited thereto. The convex lens 183 is mounted to the convex lens holding part 185 forward of the tubular member 180.

[Simplified Close-Up Imaging Device]

Figure 14:
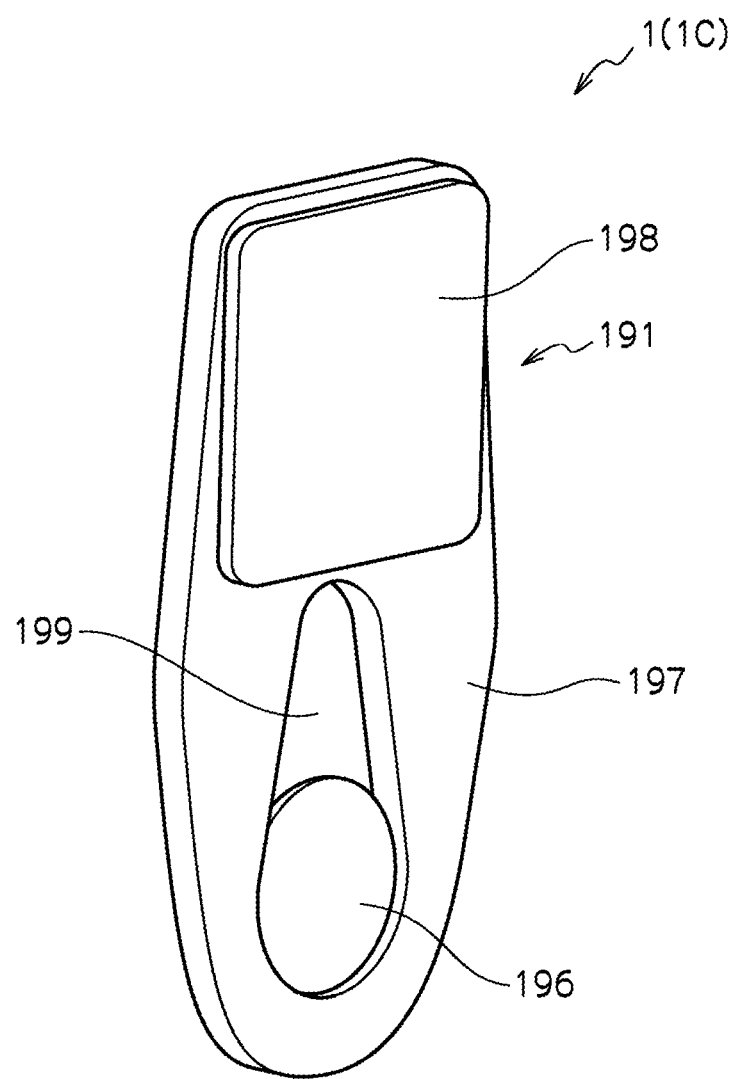
FIG. 14 is a simplified close-up imaging device including a convex lens member and a color filter member.
Figure 15A:
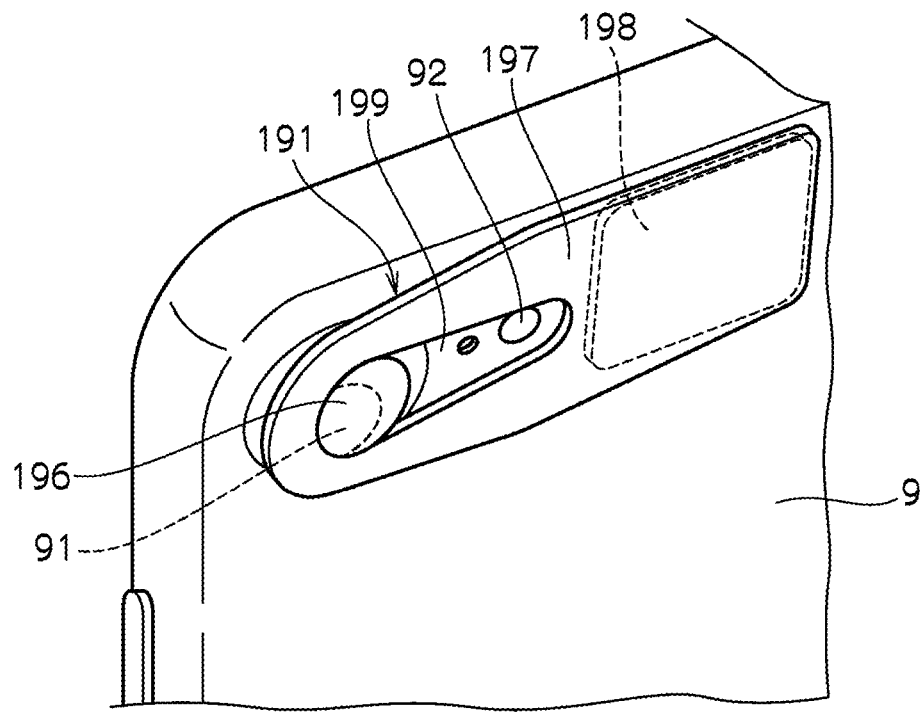
FIGS. 15A and 15B are explanatory views of modes in which the simplified close-up imaging device illustrated in FIG. 14 is mounted.
Figure 15B:
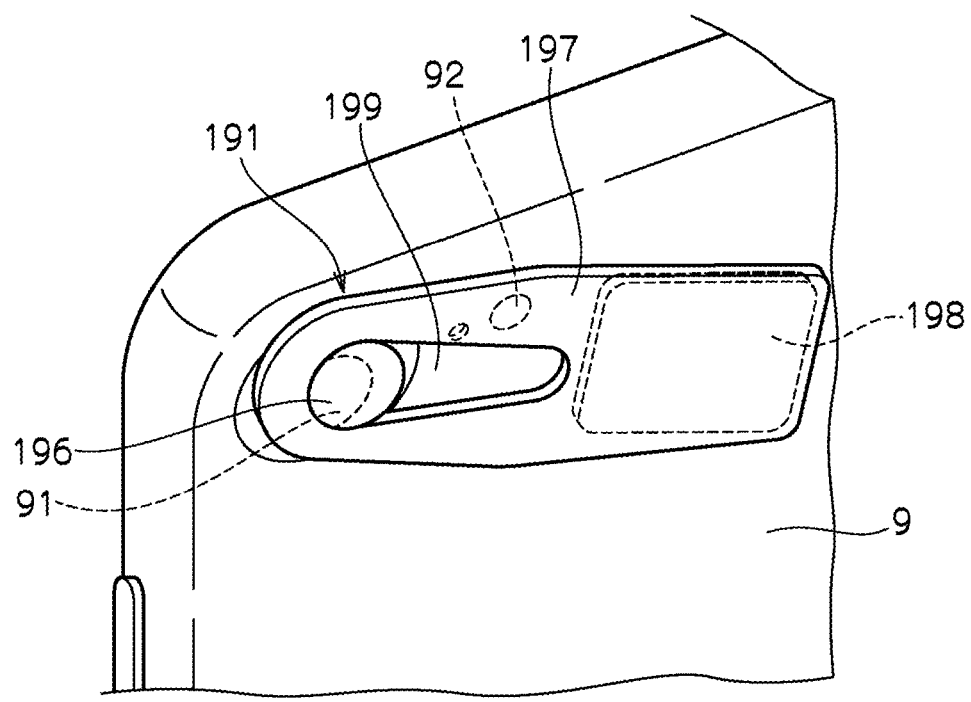

A close-up imaging device 1C according to the present invention may be a simplified close-up imaging device 191. As illustrated in FIG. 14, this simplified close-up imaging device 191 includes a convex lens member 196 and a color filter member 197; Reference numeral 199 denotes an opening, and this opening 199 is provided so as to cover or uncover the light source 92, as illustrated in FIGS. 15A and 5B. Reference numeral 198 denotes an adhesive member, and this adhesive member 198 is provided so as to slide while adhered to the smartphone 9. The effect of the present invention can be realized by such a simplified close-up imaging device 191 as well.

As described above, it is possible to easily mount the close-up imaging devices 1B, 1C according to the present invention to the smartphone 9 as external attachments to serve as a "smart eye camera." Such a smart eye camera can capture all still images and moving images obtained from an ophthalmic examination of a patient. Furthermore, the smart eye camera is significantly inexpensive compared to a slit lamp biomicroscope or a handheld slit lamp biomicroscope, making it easy to prepare a plurality of devices and, by using a device prepared for animals separately from human clinical use, it is possible to capture still images and moving images of the eyes of experimental animals (animal models), companion animals such as pets, and reared animals in zoos, and acquire ophthalmic findings of the animals as well.

Furthermore, the smart eye camera is available for clinical use with humans. Specifically, in ophthalmic examinations to date, the examination is performed with the patient fixed to a provided stand. Therefore, medical examinations for children and the bedridden elderly require expert skills. However, in the smart eye camera, the element of "recording" is added to the portable medical instrument, and recorded still images or moving images can be shared among medical personnel. Furthermore, the smart eye camera can be expected to improve the diagnostic accuracy of ophthalmologists by analyzing the data by AI as big data. Then, finally, the smart eye camera is used as a self-diagnostic tool by all smartphone users, making it possible to further develop the ophthalmic examination itself.

The smart eye camera is conceivably used in an ophthalmic examination, but is not limited thereto. For example, the smart eye camera may be used not only in an ophthalmic outpatient clinic, but also in a place other than an ophthalmic clinic, such as a medical examination place, a long-term care health facility for the elderly, an ambulance, and a science, health, or medical school class. In addition, the smart eye camera can also be used in animal-related facilities such as an animal hospital, a zoo health center, and a research institute as well.

EXAMPLES

Hereinafter, the present invention will be describe in more detail using demonstration examples. Tear film break-up time (TFBUT) is an essential parameter used for the diagnosis of dry eye disease (DED), but a method for investigating TFBUT in a mouse model has not yet been established. The close-up imaging device 1 according to the present invention is an innovative device called a "smart eye camera" and, with this smart eye camera, several conventional problems were solved, and TFBUT was evaluated in a DED mouse model. In Demonstration Example 1 below, in a DED mouse model related to graft-versus-host disease, images captured by an existing device and the smart eye camera (close-up imaging device) according to the present invention were compared, and an eye examination, including TFBUT, of the mouse model was conducted. Further, in Demonstration Example 2, examinations pertaining to the imaging of the anterior eye and the imaging of the eye ground of humans were conducted. Furthermore, in Demonstration Example 3, TFBUT measurements, which are diagnostic criteria for dry eye, were performed on a total of 42 patients including patients with dry eye and normal patients without dry eye.

Demonstration Example 1

DED is caused by a decrease in tear volume, rapid collapse of the tear film, and an increase in tear evaporation, and TFBUT is one of the core mechanisms of DED. Although the DED mouse model has been studied in past DED research, a method for measuring TFBUT in humans has not been established with the DED mouse model. There are several reasons why TFBUT evaluation in a mouse model cannot be applied to humans as is. First, a width of the cornea of a mouse is only 2 to 3 mm and the size is so small, and thus it is difficult to adjust the focus for human application. Second, a clinical slit lamp biomicroscope is used for an examination of the anterior eye (cornea, lens), but the device is so large, and thus cannot be easily moved and does not have an image recording function. Third, existing slit lamp biomicroscopes are expensive and have low cost effectiveness. To avoid these problems, usage of tear secretion (TS) and corneal fluorescein score (CFS) for diagnosis in the DED mouse model has increased. However, in such a DED mouse model as well, a device easily applicable to humans has not yet been established.

The close-up imaging device according to the present invention can be mounted to a smartphone as a portable attachment to serve as a "smart eye camera." The close-up imaging device according to the present invention can be connected to a smartphone to capture an image or video of an eye, is capable of adjusting the focus, is portable, includes a recording device, is low cost, and is highly cost-effective. Hereinafter, the close-up imaging device is demonstrated with this new DED mouse model.

(Configuration of Close-Up Imaging Device)

The close-up imaging device 1 includes the detachable convex lens 96 (focal length: 10 to 30 mm, magnification: 20×) above the camera lens 91 of the smartphone 9 for focus adjustment. While this convex lens 96 is not particularly limited, in this demonstration example, TK-12P (manufactured by TSK Co., Ltd.) was used. Further, the detachable blue color filter member 97 is provided above the light source 92 of the smartphone 9 in order to convert white light into blue light having a wavelength of 488 nm. While this blue color filter member 97 is not particularly limited, in this demonstration example, an acrylic resin blue filter (PGZ 302K 302, manufactured by Kuraray Co., Ltd.) was adopted. Furthermore, above the convex lens 96, a detachably provided band-pass filter (trade name: CC G50, manufactured by Fujifilm Corporation) for wavelengths of 525 to 550 nm was provided. By providing this filter, it is possible to utilize the close-up imaging device 1 to enhance a reflection excited by the fluorescein solution administered into the eye by eyedrops. It should be noted that an illuminance of a digital lux illuminator (model name: LX-1010B, manufactured by Zhangzhou WeiHua Electronic Co., Ltd.) of the smartphone 9 used this time was 8,000 lux without a blue filter and 2,000 lux with a blue filter. The smart eye camera used is a model designed for iPhone 7 and is the device illustrated in FIG. 5 to FIG. 13.

Figure 16:
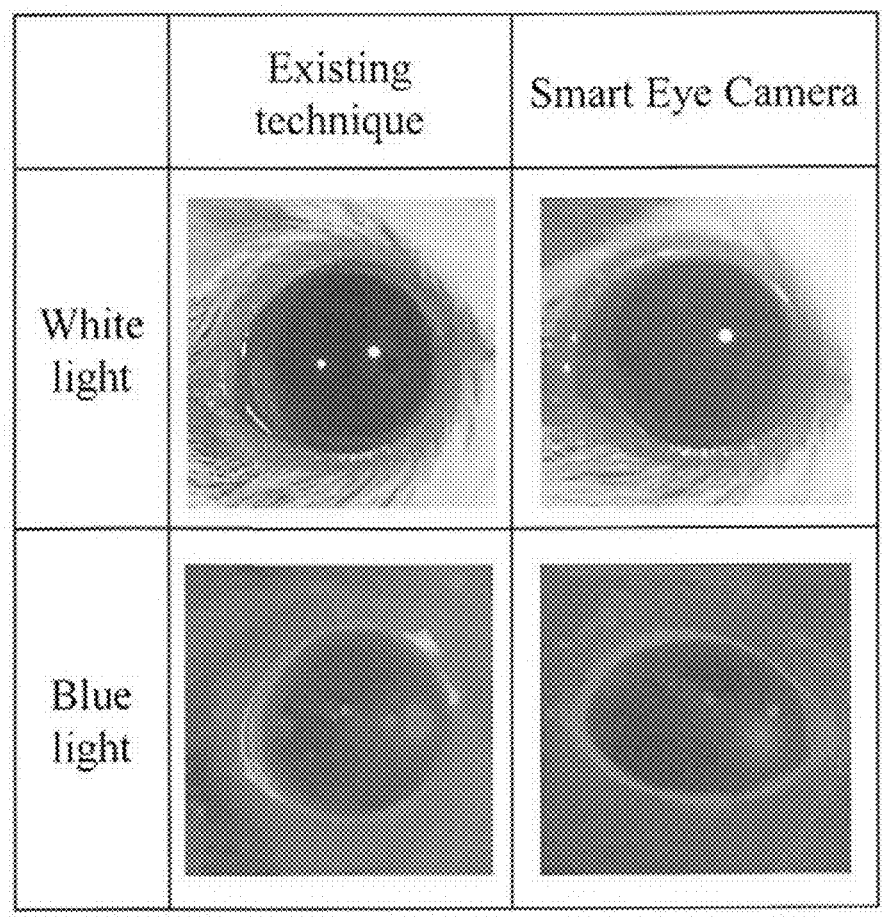
FIG. 16 shows, in the upper row, representative photographs of an eye exposed to white light and, in the lower row, representative photographs of fluorescein staining. The images in the left column, are examples of an eye captured with an existing device, and the images in the right column are examples of an eye captured using a smart eye camera.

FIG. 16 shows, in the upper row, representative photographs of an eye exposed to white light and, in the lower row, representative photographs of fluorescein staining. In FIG. 16, the images in the left column are examples of an eye captured with an existing device, and the images in the right column are examples of an eye captured using the smart eye camera. It should be noted that, as the existing device, a device widely used for evaluating the eye of the ED mouse model was used. Specifically, a device configured by a microscope (product name: SZ61), a camera. (product name: DP70), and a light source (product name: LG-PS2) manufactured by Olympus Corporation, and a portable slit lamp biomicroscope (product name: SL-15, Kowa Co., Ltd.) was used.

(Mouse GVHD Group-Related DED Model)

For the DED mouse model, the method by Zhang for reproducing the GVHD group-related DED phenotype was selected, similar to the clinical example. The used B10.D2 and BALB/cCrSlc (BALB/c) mice (7 weeks old) were purchased from Sankyo Research Laboratories (Tokyo, Japan). After being adapted to a specific pathogen free (SPF) environment for one week, the mice were divided into three groups (five mice per group). For the DED (GVHD group model) group, allogeneic bone marrow transplantation (BMT) was performed by using 8-week-old male B10.D2 and female BALB/c mice for the donors and recipients. For the negative control (non-GVHD group), syngeneic BMT was performed by transplanting donor cells from male BALB/c mice to female BALB/c mice. Six hours prior to BMT, these recipient mice were irradiated with 700 cGy using a Gammacel 137 Cs source (Hitachi Medico Ltd.) and then donor cells were injected via tail vein injection. For a healthy control (normal group control), female BALB/c mice of the same age were selected.

Three mouse models (GVHD group, non-GVHD group, and normal group control) were used for comparison. The DED phenotype in this DED mouse model appears three weeks after BMT, and thus eyeball phenotypes such as body weight, TFBUT, corneal fluorescein score (CFS), and TS were collected once a week, from before BMT (8 weeks old) to 12 weeks old. It should be noted that all imaging data recorded by the smart eye camera were manually transferred to an iMac (Apple Inc., U.S.A.) via Bluetooth and converted to mp4 video data for safe storage.

(Evaluation of Tear Film Break-Up Time)

Stability was measured by using tear film break-up time (TFBUT). An observer gripped the mouse with one hand and then injected 1 µL of 0.5% fluorescein sodium into the conjunctival sac using a micropipette. After administering the eyedrops three times, the observer recorded an image of the eye with a first camera application using the smart eye camera illustrated in FIG. 5 with the right hand. To compare the new technique with the existing technique, the TFBUT acquired with the existing device was evaluated by a former method.

(Evaluation of Corneal Fluorescein Score)

Conical epithelial wound was evaluated by using the cortical fluorescein score (CFS) evaluated 90 seconds after administration of eyedrops of fluorescein. Each cornea was divided into four quadrants and then recorded individually. The CFS was calculated by using a four-grade evaluation. An evaluation 1 included slightly dotted staining with "<30 spots," an evaluation 2 included dotted staining with ">30 spots" without dispersed, an evaluation 3 included severe diffuse staining, but no positive plaques, and an evaluation 4 included fluorescein positive plaques.

(Evaluation of Tear Secretion)

Tear secretion (TS) was measured by using a modified Schirmer test. Phenol red thread was placed on a temporal side of an upper eyelid margin for 15 seconds. A length of a wet portion from the end was within 0.5 mm.

(Data Analysis)

Data analysis was performed with Prism software (Mac version 6.04; GraphPad Software, Inc., U.S.A.). The D'Agostino-Pearson omnibus normality test was used to evaluate whether the data exhibited a normal distribution. The Mann-Whitney U test was used to compare the differences between normal and objective ((GVHD group and non-GVHD group) in several parameters including body weight, TFBUT, CFS, and TS. The Wilcoxon signed-rank test was used to compare the differences between results valuated by the existing technique and the smart eye camera. Friedman test was used to compare the differences in TFBUT evaluations by three different eye specialists, captured with the smart eye camera. Lin's concordance correlation coefficient was used to evaluate the possible correlation between TFBUT and CFS using the existing technique and the smart eye camera. Data were expressed as the mean±standard deviation (SD), and P values less than 0.05 were regarded as statistically significant.

[Results]

(Body Weight)

Figure 17A:
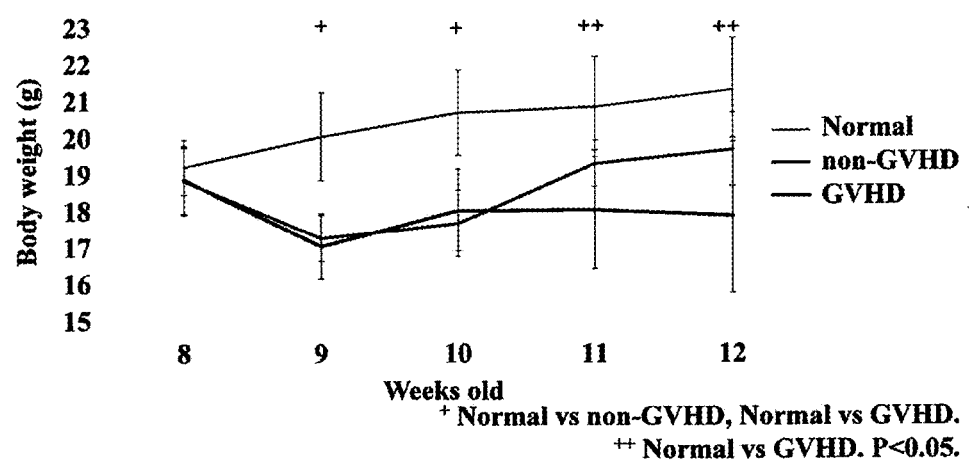
FIG. 17A is a graph showing results obtained by measuring a relationship between age (weeks old) and body weight of mice.

FIG. 17A is a graph showing results obtained by measuring a relationship between age (weeks old) and body weight of mice, and FIG. 17B is a table of progress of the body weight by group (green: normal group, blue: non-GVHD group, red: GVHD group). To demonstrate the applicability of the smart eye camera in a mouse model of mice, bone marrow transplantation (BMT) was first evaluated. Based on the results of FIGS. 17A and 17B, the body weight of the mice was initially adjusted for each group, and therefore there was no difference in body weight between the normal group, the non-GVHD group, and the GVHD group before BMT (8 weeks old). However, in the 9- and 10-week-old non-GVHD group and GVHD group, the body weights were significantly reduced compared to the normal group. As a result, the body weights were P=0.016 and 0.016 at 9 weeks old, and P=0.016 and 0.032 for the normal group vs. the non-GVHD group and the normal group vs. the GVHD group respectively, at 10 weeks old. The body weights were P=0.032 and 0.032 for the GVHD group at 11 and 12 weeks old, respectively, when compared to the body weights for the normal group at 11 and 12 weeks old, and reduced only in the GVHD group.

(Volume of Tear Secretion)

FIG. 18A is a graph showing results obtained by measuring a relationship between age (weeks old) and tear secretion (TS) volume of mice, and FIG. 18B is a table of progress of continuing tear secretion (TS) by group (green: normal group, blue: non-GVHD group, red: GVHD group). Significant differences in TS were observed between the normal group and the non-GVHD group and between the normal group and the GVHD group, at 9 to 12 weeks old. Furthermore, at 12 weeks old, TS was significantly shorter in the GVHD group compared to the iron-GVHD group, Given N=5 per group, the evaluation of significance (P<0.05) was performed by the Mann-Whitney U test.

Based on the results in FIGS. 18A and 18B, while there was no difference in TS before BMT for body weight, these values were significantly reduced in the non-GVHD group and the GVHD group compared to the normal group at 9 to 12 weeks old. The normal group, vs, the non-GVHD group and the normal group vs. the GVHD group were P===0.008 and 0.016 at 9 weeks old, =0.008 and 0.008 at 10 weeks old, P=0.016 and 0.024 at 11 weeks old, and P=0.008 and 0.008 at 12 weeks old, respectively. Further, the TS volume in the GVHD group at 12 weeks old was 1.65±1.01, which was significantly low compared to the 3.70±0.33 of the non- GVHD group. Furthermore, the non-GVHD group vs. the GVHD group at that time was P=0.008.

(Tear Film Break-Up Time)

FIG. 19A is a graph showing results obtained by measuring a relationship between age (weeks old) and tear film break-up time (TFBUT) of mice, and FIG. 19B is a table of progress of TFBUT by group (green: normal group, blue: non-GVHD group, red: GVHD group). Significant difference was obtained by using the Mann-Whitney U test given n=5 per group and P<0.05 as significant. TFBUT was evaluated by using the right eye.

For TFBUT, no difference was observed between the normal group, the non-GVHD group, and the GVHD group before BMT (8 weeks old). However, TFBUT was significantly reduced in the GVHD group (P=0.024, 0.008, and 0.008 at 10, 11, and 12 weeks old, respectively) when compared to the normal group at 10 to 12 weeks old. TFBUT was reduced in the non-GVHD group as well when compared to the normal group at 11 weeks old (normal group vs, non-GVHD group was 5.80±0.84 vs 4.00±0.71, P=0.024). Furthermore, the GVHD group had a significantly shorter TFBUT than the non-GVHD group (P=0.040 and 0.008 at 11 and 12 weeks old, respectively) at 11 and 12 weeks old when compared to the post-BMT group.

FIG. 20 shows continuous tear film photographs stained by a fluorescein solution. Thus, breakup of the tear film was observed. FIG. 20 shows, in the upper row, examples of the GVHD group in which the tear film was broken in three seconds (TFBUT=three seconds) and in the lower row, examples of the normal group in which the tear film was stabilized in three seconds and collapsed in six seconds (TFBUT=six seconds). The photographs show the right eyes of 12-week-old female BALB/c mice. These results show that the smart eye camera can evaluate continuous TFBUT of the GVHD group DED mouse model.

(Continuous Corneal Fluorescein Score)

FIG. 21A is a graph showing results obtained by measuring a relationship between age (weeks old) and continuous corneal fluorescein score (CFS) of mice, and FIG. 21B is a table of progress of CFS by group (green: normal group, blue: non-GVHD group, red: GVHD group). Significant difference was obtained by using the Mann-Whitney U test given n=5 per group and P<0.05 as significant. CFS was evaluated by using the right eye.

When compared with the normal group at 9, 11, and 12 weeks old, a significant difference was observed in the GVHD group (P=0.008, 0.008, and 0.032, respectively), as shown in FIG. 21B. While the non GVHD group tended to have a higher CFS than the normal group, and the GVHD group tended to have a higher CFS than the non-GVHD group, these differences did not reach statistical significance (all P>0.05). From this result, it was understood that continuous CFS can also be evaluated by the smart eye camera in the DED mouse model of the GVHD group.

(Comparison with Existing Device)

FIGS. 22A to 22C show results of comparing the TFBUTs and CFSs of the new technique (smart eye camera) of the close-up imaging device according to the present invention and the existing technique, FIG. 22A being a graph of TFBUT, FIG. 22B being a graph of CFS, and green indicating normal group, blue indicating non-GVHD group, and red indicating GVHD group. FIG. 22C is a table. Significant difference was obtained by using the Mann-Whitney U test given n=5 per group and P<0.05 as significant.

In each graph, two bars are aligned. From this, it is understood that there is no significant difference between the use of the existing device and the smart eye camera in ordinary non-GVHD groups and GVHD groups. Then, for TFBUT, based on the results obtained by the smart eye camera and the portable slit lamp biomicroscope (existing device), there was no significant difference between the normal group control, the non-GVHD group, and the GVHD group (0.50, 0.99, and 0.99, respectively, and all P>0.05). Similarly, for CFS, based on the results obtained by the smart eye camera and the existing device, significant differences were not found between the normal group control, the non-GVHD group, and the GVHD group (P=0.99, 0.75, and 0.50, respectively, and all P>0.05).

Figure 23B:
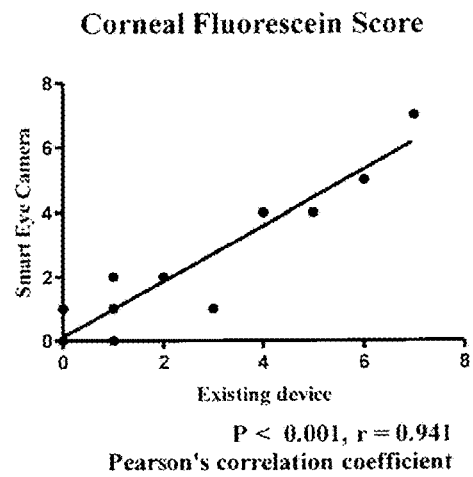
Figure 24A:
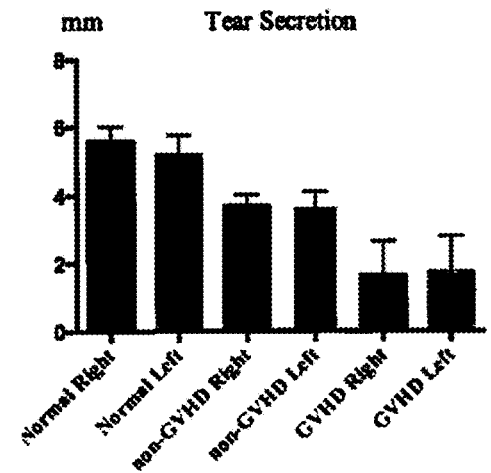
FIGS. 24A to 24D are graphs summarizing body weight loss, shortening of TS, and worsening of corneal epithelitis.
Figure 24B:
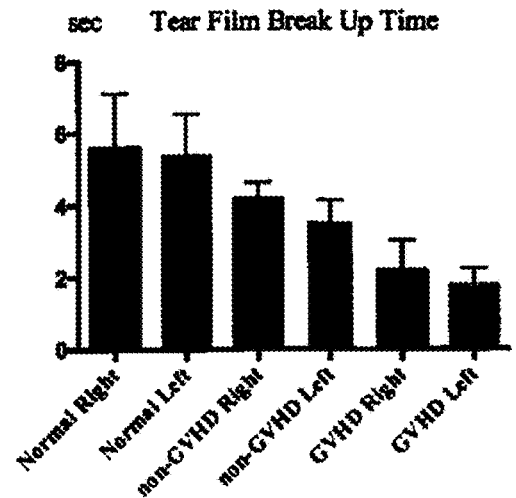
Figures 24C, 24D:
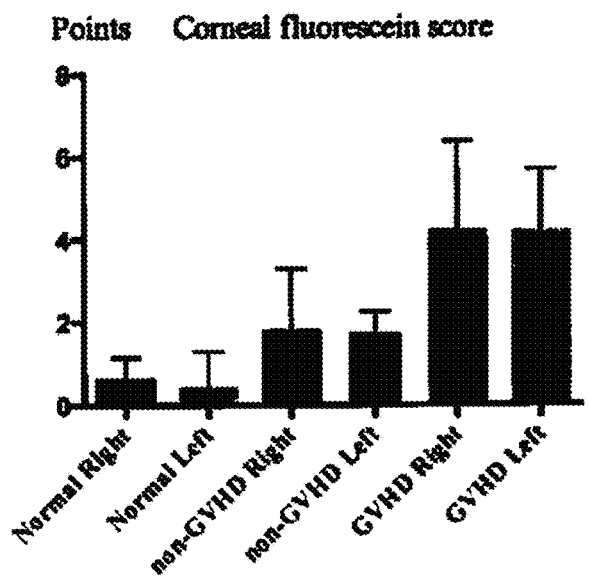
Figure 25A:
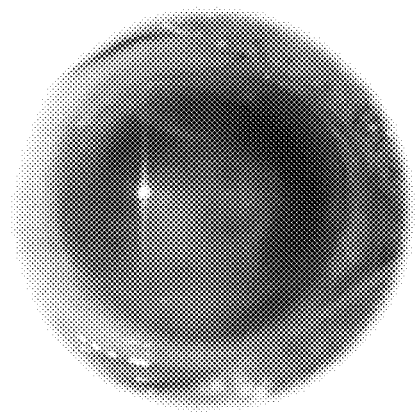
FIGS. 25A to 25F are captured images, FIG. 25A being corneal opacity, FIG. 25B being post cataract surgery, FIG. 25C being epidemic conjunctivitis, FIG. 25D being no cataracts, FIG. 25E being moderate cataracts, and FIG. 25F being severe cataracts.
Figure 25B:
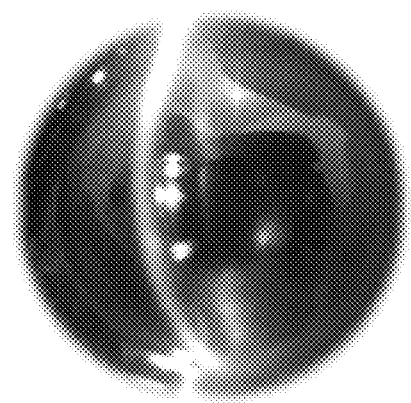
Figure 25C:
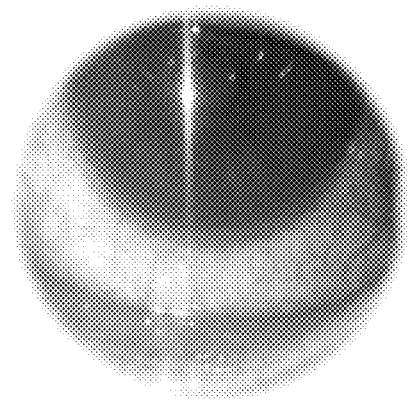
Figure 25D:
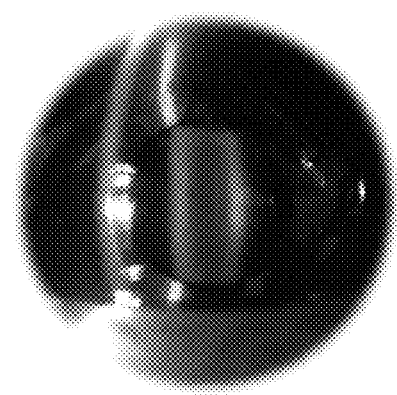
Figure 25E:
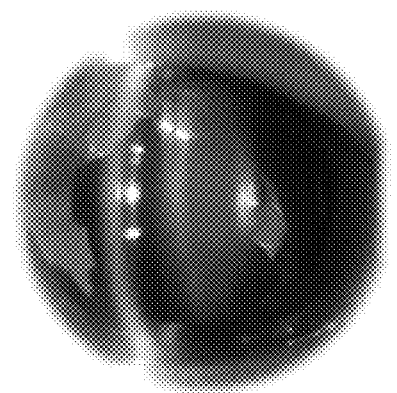
Figure 25F:
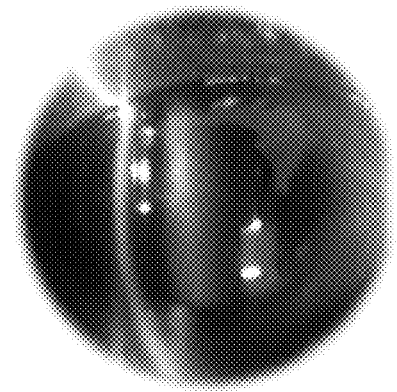

FIGS. 23A and 23B are graphs showing a correlation between the smart eye camera according to the present invention and the existing device, FIG. 23A being a graph of TFBUT and FIG. 23B being a graph of CFS. In each graph, the Y axis indicates the numerical value evaluated by the smart eye camera, the X axis indicates the evaluation by the existing device, and n=15. A high correlation was observed in TFBUT (R=0.868, 95% CI: 0.656 to 0.953) and CFS (R=0.934, 95% CI: 0.823 to 0.976).

Based on the result of FIG. 23A, the TFBUTs of the smart eye camera and the existing device were P<0.001 and r=0.871, exhibiting a significant correlation. Further, based on the result of FIG. 23B, the CFSs of the smart eye camera and the existing device were also P<0.001 and r=0.941 exhibiting a significant correlation. These results show that, compared to the existing device, the smart eye camera has the same quality as when the eyeball phenotypes of the mouse model are adapted.

(Conclusion)

Based on the above demonstration example, the applicability of the present invention in the DED mouse model could be demonstrated. This model was characterized by body weight loss, shortening of TS, and worsening of the corneal epithelitis, and reflected in the CFS. FIGS. 24A to 24D are graphs summarizing these. Based on the results, the TFBUT of the GVHD group in the DED mouse model was reduced compared to the normal group and the non-GVHD group. As shown in FIGS. 24A to 24D, this exhibits that the TFBUT trend is similar to the TS trend and opposite to the CFS trend.

As shown in FIGS. 22A to 22C, there was no difference between the smart eye camera and the existing device. Further, as understood from the correlation analysis shown in FIGS. 23A and 23B, the results obtained by the smart eye camera and the existing device exhibited a significantly high correlation for both TFBUT and CFS. These results mean that the results captured with the smart eye camera have the same quality as the results captured with the existing device. Furthermore, although not illustrated, similar results were obtained by different observers as well.

Demonstration Example 2

The present inventors conducted observations using the smart eye camera in December 2018. The cases were anterior eye: 58 eyes (21 males, 37 females), and eye ground: 41 eyes (19 males, 22 females). The items examined included presence or absence of eyelid or anterior eye disease, severity of cataracts, and the like as the anterior eye, presence or absence of an optic nerve abnormality, presence or absence of eye ground disease, and the like as the eye ground, and left and right differences, number of seconds for imaging, and the like as other items.

(Observation of Anterior Eye)

The anterior eye was evaluated upon capturing an image thereof using the smart eye camera illustrated in FIG. 8 to FIG. 10. As shown in FIGS. 25A to 25F, various anterior eye diseases such as pterygium, corneal opacity, epidemic keratoconjunctivitis, and intraocular lens could be evaluated in all cases. FIGS. 25A to 25F are captured images, FIG. 25A being corneal opacity, FIG. 25B being post cataract surgery, FIG. 25C being epidemic conjunctivitis, FIG. 25D being no cataracts, FIG. 25E being moderate cataracts, and FIG. 25F being severe cataracts. The severities of cataracts evaluated with the existing medical device and with the smart eye camera were the same. Thus, various symptoms of the anterior eye can be observed by the smart eye camera serving as the close-up imaging device according to the present invention.

Figure 26:
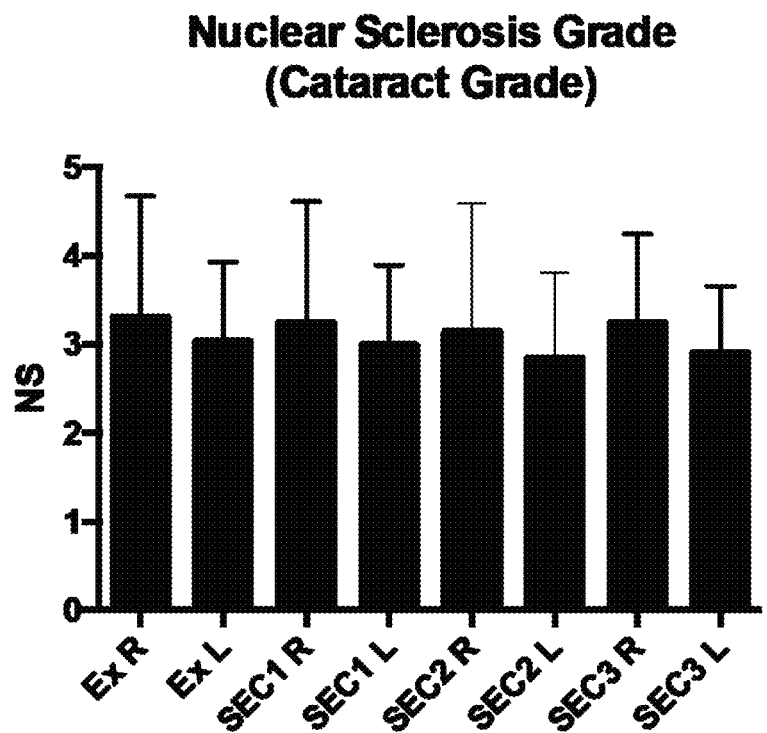
FIG. 26 shows a result of evaluation of nuclear sclerosis (cataracts) by the smart eye camera.
Figure 27:
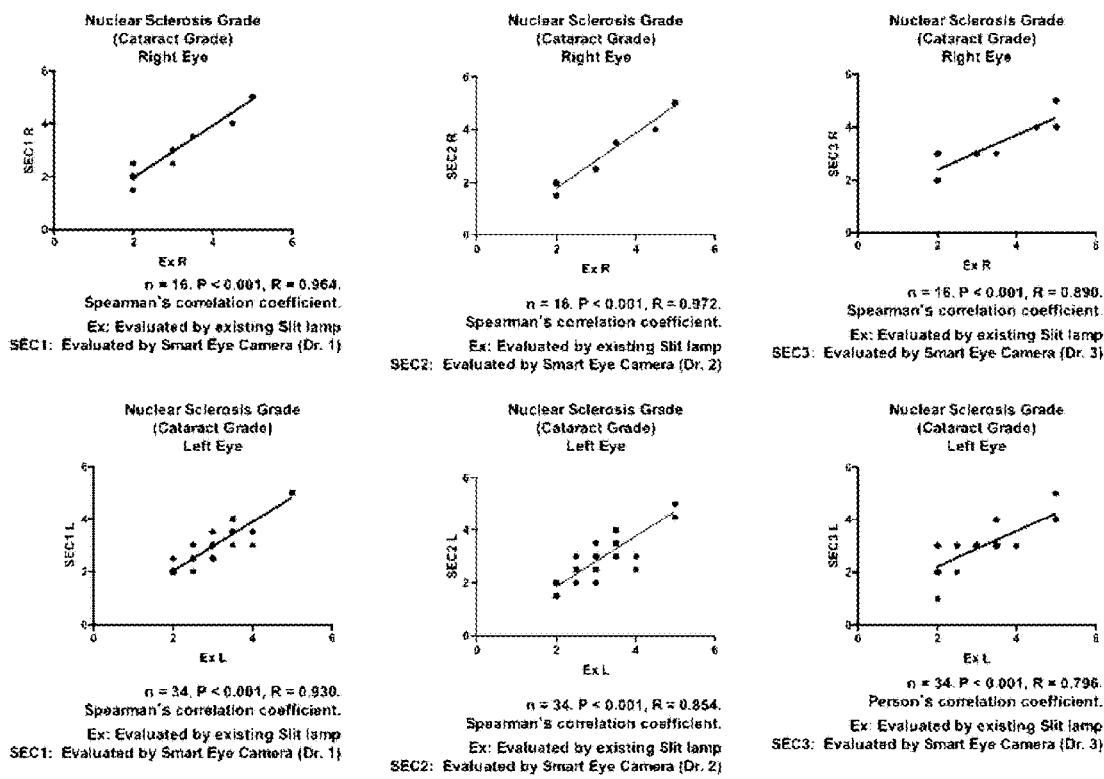
FIG. 27 shows a result of correlation between the smart eye camera and an existing device by each eye specialist.

In FIG. 26 and FIG. 27, the evaluation and correlation of nuclear sclerosis (cataracts) by the smart eye camera illustrated in FIG. 8 to FIG. 10 were evaluated. In FIG. 26, the vertical axis is the NS grade that indicates the degree of cataract hardening, and the horizontal axis is the EX, which is the evaluation result using the existing device, and SECs 1 to 3, which are the results obtained by three eye specialists who conducted evaluations with the smart eye camera. There were no significant differences among any observers or in the left and right eyes as well. Further, FIG. 27 is a result of correlation between the smart eye camera and the existing device by each eye specialist. A correlation between the smart eye camera and the existing device was found, and a high correlation was observed for the left and right eyes as well. These results show that the smart eye camera illustrated in FIG. 8 to FIG. 10 has sufficient objectivity and reproducibility for adapting eye phenotypes.

(Observation of Eye Round)

Figure 28A:
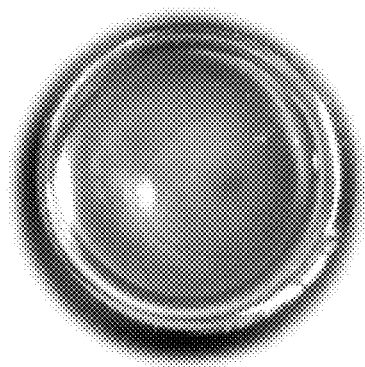
Figure 28B:
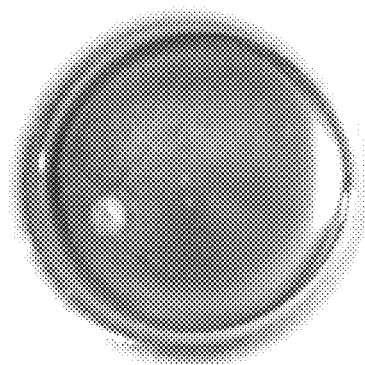
Figure 28C:
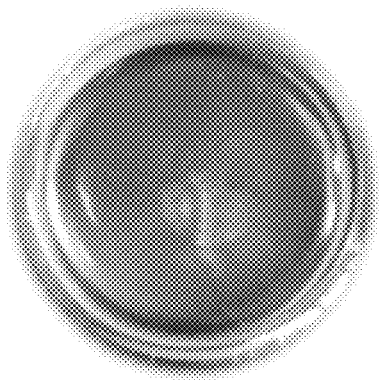

FIGS. 28A to 28D are imaging results of eye grounds, FIG. 28A being a normal eye ground FIG. 28B being hypertensive retinopathy, FIG. 28C being retina thinning and FIG. 28D being optic disc cupping and expansion (suspected glaucoma). The smart eye camera was able to evaluate the eye ground in 85% or more cases, including the examples of FIGS. 28A to 28D. It should be noted that the cases impossible to evaluate were opacities of an optic media, such as severe cataracts, but cannot be evaluated even with the existing device. The smart eye camera used here was a smart eye camera with the tubular member 180 illustrated in FIG. 11 to FIG. 13 mounted thereto, and observation and imaging of the eye ground can be preferably performed.

FIG. 29 is a correlation between doctors in relation to hypertensive retinopathy evaluated by the smart eye camera. There was no large difference between the doctors. Further, the glaucoma diagnosis rates were also 25.7% and 18.9% among the doctors, having no large difference regarding this as well. The smart eye camera used here was also a smart eye camera with the tubular member 180 illustrated in FIG. 11 to FIG. 13 mounted thereto, and observation and imaging of the eye ground can be preferably performed.

In this Demonstration Example 2, an ophthalmic examination using the smart eye camera was performed. Both the anterior eye and the eye ground were considered useful for comparison with the existing device and evaluation among the doctors. The average imaging time was 16.5±5.1 seconds for the anterior eye and 27.5±12.8 seconds for the eye ground, which was a short examination time even when compared to approximately 240 seconds in an examination using the existing device. Further, no left-right difference was fund, and both eyes could be evaluated to the same degree.

The close-up imaging device according to the present invention is capable of reproducibly examining eye-related tissues of the conjunctiva, eyeball, eyelid, lacrimal gland, and the like. Furthermore, this smart eye camera can be converted for human use.

Demonstration Example 3

Figure 30:
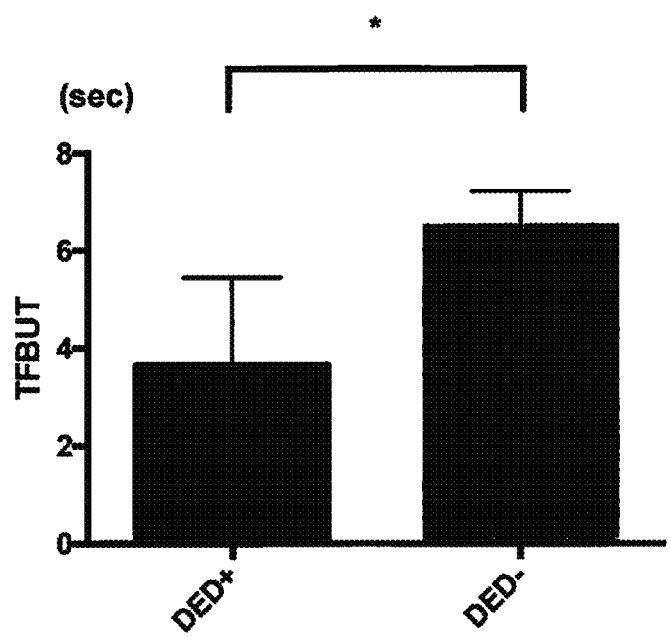
FIG. 30 shows TFBUT measurement results, which are diagnostic criteria for dry eye, for a total of 42 patients including patients with dry eye and normal patients without dry eye.

In Demonstration Example 3, TFBUT measurements, which are diagnostic criteria for dry eye, were performed on a total of 42 patients including patients with dry eye and normal patients without dry eye using the close-up imaging device 1B illustrated in FIG. 5 to FIG. 13. The results are shown in FIG. 30. The TFBUT of the dry eye patient group (represented by "DED+") was 3.64±1.81 seconds, and the TFBUT of the normal patients without dry eye (represented by "DED−") was 6.50±0.71 seconds. Statistically significantly, the dry eye group resulted in a shorter TFBUT. A significant difference was obtained by using the Mann-Whitney U test with $P<0.05$ as significant. From this, it can be said that the smart eye camera is capable of evaluating eye findings such as TFBUT.

As described above, it was understood that the smart eye camera serving as the close-up imaging device according to the present invention can evaluate continuous eye phenotypes such as TFBUT and CFS. This new technique can be expected to be applied to human clinical use. Then, this smart eye camera can be expected to contribute to the healthcare industry by taking advantage of the use of smartphones.

DESCRIPTIONS OF REFERENCE NUMERALS 1, 1B, 1C Close-up imaging device
2 Polarizing filter (vertically polarized light)
3 Polarizing filter (horizontally polarized light)
4 Color filter (orange)
8 Plate-shaped filter
9 Smartphone
10 Housing
11 Outer wall part
12 Front wall (First optical path forming part, Second optical path forming part)
13 Back wall
14 Left side wall
15 Right side wall
16 Upper wall
17 Lower wall
21 First partition wall part (Second optic path forming part)
22 Second partition wall pan (First optical path forming part)
30 First plate-shaped mirror (Second optical path forming part, Reflecting member, Optical path switching part)
31 Hinge
40 Second plate-shaped mirror (Second optical path forming part, Irradiation position adjusting part)
41 Right side knob
42 Left side knob
50 Lens part (Second optical path forming part, Focus adjusting part)
51 Convex lens
52 Convex lens folder
53 Lens part knob
60 Bellows part (Optical path switching part)
70 Slit forming part (Second optical path forming part)
71 Slit plate
72 Movable plate
101 Incoming light opening 102 First outgoing light opening
103 Second outgoing light opening
141 Filter insertion slit
142 Filter insertion groove
151 Right all guide concave twin
161 Groove extending in forward-rearward direction
162 Groove extending in leftward-rightward direction
163 Groove extending in leftward-rightward direction
171 Terminal insertion opening
211 First partition guide concave part
721 Rotary knob
A First optical path
B Second optical path
61 Slit light forming member
61' Main body part
62 Cylindrical lens
63 Upper holding member
64 Lower holding member
65 First reflecting mirror
66 Second reflecting mirror
67 Slit
68 Mounting pint
69 Step part
80 Housing
81 Outer wall part
82 Front wall
83 Back wall
84 Left wall
85 Right wall
86 Upper wall
87 Lower wall
88 Hole of front wall
90 Front surface plate
90a Opened left edge portion
90b Right edge portion
90c Upper edge portion
90d Lower edge portion
91 Camera lens
92 Light source
93 Convex lens member
94 Convex lens mounting hole
95 Hole
96 Convex lens
97 Color filter member
98 Hole
180 Tubular member
181 Mounting part
182, 182a, 182b Tube part
183 Convex lens
184 Opening
185 Convex lens holding part
186 Mounting part
191 Simplified close-up imaging device
196 Convex lens
197 Color filter part
198 Adhesive member
199 Opening

What is claimed is:

1. A close-up imaging device detachably mounted to a mobile terminal equipped with a light source and a camera lens for imaging, comprising:
a plate-shaped color filter member detachably provided above the light source; and
a plate-shaped convex lens member detachably provided above the camera lens for imaging are slidably fitted into rails of the close-up imaging device, wherein
the plate-shaped color filter member or the plate-shaped convex lens member being fitted into rails of the close-up imaging device is attached and detached from above the light source or camera lens for imaging, by sliding the leftward-rightward direction, and
imaging of an anterior eye being performed by sliding the rails for removing the color filter member and attaching the convex lens member, and
observation of an injury of the anterior eye being performed by sliding the rails for attaching the color filter member and the convex lens member; wherein
the rails comprise a front wall of the close-up imaging device and mounted to a convex peripheral edge portion of the front wall and a front surface plate provided inside the convex peripheral edge portion.

2. The close-up imaging device according to claim 1, further detachably comprising:
a slit light forming member that forms light from the light source into slit light by a cylindrical lens.

3. The close-up imaging device according to claim 2, wherein
the slit light forming member includes a first reflecting mirror and a second reflecting mirror that reflect the light from the light source, and a slit part that allows the light reflected by the first reflecting mirror and the second reflecting mirror to pass therethrough, and
the light that passes through the slit part becomes slit light by the cylindrical lens.

4. A close-up imaging device detachably mounted to rails of a mobile terminal equipped with a light source and a camera lens for imaging, comprising:
a color filter member detachably provided above the light source; and
a convex lens member detachably provided above the camera lens slidably fitted into rails of the close-up imaging device,
imaging of an anterior eye being performed by removing the color filter member and attaching the convex lens member, and
observation of an injury of the anterior eye being performed by attaching the color filter member and the convex lens member, further detachably comprising:
a slit light forming member that forms light from the light source into slit light by a cylindrical lens; wherein
the rails comprise a front wall of the close-up imaging device and mounted to a convex peripheral edge portion of the front wall and a front surface plate provided inside the convex peripheral edge portion.

5. The close-up imaging device according to claim 4, wherein
the tubular member includes a color filter member and a polarizing filter in an optical path of outward light emitted from the light source, and another polarizing filter in an optical path of inward light reflected by the eye ground.

6. The close-up imaging device according to claim 1 further detachably comprising:
a tubular member including a convex lens at a tip end thereof.

7. The close-up imaging device according to claim 6, wherein
the tubular member includes a color filter member and a polarizing filter in an optical path of outward light emitted from the light source, and another polarizing filter in an optical path of inward light reflected by the eye ground.

8. The close-up imaging device according to claim 4, further detachably comprising:
   a tubular member including a convex lens at a tip end thereof.

9. The close-up imaging device according to claim 4, wherein
   the slit light forming member includes a first reflecting mirror and a second reflecting mirror that reflect the light from the light source, and a slit part that allows the light reflected by the first reflecting mirror and the second reflecting mirror to pass therethrough, and
   the light that passes through the slit part becomes slit light by the cylindrical lens.

10. The close-up imaging device according to claim 9, wherein
    the light that passes through the slit part becomes slit light by the cylindrical lens and is irradiated to the anterior eye portion, and
    the light reflects by the anterior eye portion internal structure of the anterior eye portion is observed or imaged by irradiating from an angle.

* * * * *